United States Patent
Moreno et al.

(10) Patent No.: US 11,576,816 B2
(45) Date of Patent: Feb. 14, 2023

(54) OPTHALMIC MICROSURGICAL INSTRUMENT

(71) Applicants: Jesus Moreno, Newark, CA (US);
Philip Ian Prosser, Prospect (AU)

(72) Inventors: Jesus Moreno, Newark, CA (US);
Philip Ian Prosser, Prospect (AU)

( * ) Notice: Subject to any disclaimer, the term of this patent is extended or adjusted under 35 U.S.C. 154(b) by 120 days.

(21) Appl. No.: 16/145,119

(22) Filed: Sep. 27, 2018

(65) Prior Publication Data
US 2019/0110925 A1    Apr. 18, 2019

Related U.S. Application Data

(63) Continuation-in-part of application No. 15/892,833, filed on Feb. 9, 2018.
(Continued)

(51) Int. Cl.
*A61F 9/007*    (2006.01)
*A61B 90/30*    (2016.01)
(Continued)

(52) U.S. Cl.
CPC .......... *A61F 9/00781* (2013.01); *A61B 90/30* (2016.02); *A61F 9/0017* (2013.01);
(Continued)

(58) Field of Classification Search
CPC .............. A61B 3/0008; A61B 17/3415; A61B 17/3421; A61B 90/30; A61B 2090/306;
(Continued)

(56) References Cited

U.S. PATENT DOCUMENTS 5,263,937 A * 11/1993 Shipp ................. A61B 17/3417
                                                                                          606/167
5,517,997 A * 5/1996 Fontenot ................. A61B 90/36
                                                                                          600/473

(Continued)

OTHER PUBLICATIONS

B. Cameron et al., "Circumferential viscodilation of Schlemm's canal with a flexible microcannula during non-penetrating glaucoma", Digital Journal of Opthomology, vol. 12, No. 1 Mar. 15, 2006.

(Continued)

*Primary Examiner* — Jocelin C Tanner
(74) *Attorney, Agent, or Firm* — GSS Law Group; Gregory S. Smith; Phillip M. Wagner

(57) ABSTRACT

In some embodiments, a microsurgical instrument includes a trocar having a rigid, hollow shaft formed with a lumen extending from a proximal end to a distal end of the shaft. The distal end of the shaft may be shaped for tissue penetration. The instrument may further include a composite microcannula slidably engaged with the trocar in the lumen. The microcannula includes a light guide and a flexible hollow tube having an outer diameter less than an inner diameter of the lumen in the trocar. Other embodiments include placing the microcannula in the lumen of the trocar, illuminating the end of the trocar by illuminating the end of the microcannula, advancing the trocar from a selected entry point on an eye into a selected structure in the eye, and extending the illuminated end of the microcannula from the trocar into the selected structure.

12 Claims, 22 Drawing Sheets

Related U.S. Application Data

(60) Provisional application No. 62/574,136, filed on Oct. 18, 2017.

(51) Int. Cl.
*A61F 9/00* (2006.01)
*A61B 17/34* (2006.01)
*A61B 90/00* (2016.01)
*A61B 3/00* (2006.01)

(52) U.S. Cl.
CPC ...... *A61F 9/00709* (2013.01); *A61F 9/00736* (2013.01); *A61B 3/0008* (2013.01); *A61B 17/3415* (2013.01); *A61B 17/3421* (2013.01); *A61B 2090/306* (2016.02); *A61B 2090/3612* (2016.02); *A61B 2090/3945* (2016.02)

(58) Field of Classification Search
CPC ..... A61B 2090/3612; A61B 2090/3945; A61F 9/0017; A61F 9/00709; A61F 9/00736; A61F 9/00781
See application file for complete search history.

(56) References Cited

U.S. PATENT DOCUMENTS

| | | | | |
|---|---|---|---|---|
| 5,637,097 | A * | 6/1997 | Yoon | A61B 17/3417 604/164.12 |
| 6,564,087 | B1 * | 5/2003 | Pitris | A61B 1/00172 600/478 |
| 6,936,053 | B1 * | 8/2005 | Weiss | A61F 9/007 604/117 |
| 7,207,980 | B2 | 4/2007 | Christian | |
| 7,699,882 | B2 | 4/2010 | Stamper | |
| 7,931,596 | B2 | 4/2011 | Rachlin | |
| 7,967,772 | B2 | 6/2011 | McKenzie | |
| 8,034,105 | B2 | 10/2011 | Stegmann | |
| 8,123,729 | B2 | 2/2012 | Yamamoto | |
| 8,172,830 | B2 | 5/2012 | Christian | |
| 8,348,924 | B2 | 1/2013 | Christian | |
| 8,425,473 | B2 | 4/2013 | Ho | |
| 8,491,549 | B2 | 7/2013 | Conston | |
| 10,987,247 | B2 * | 4/2021 | Moreno | A61F 9/00736 |
| 2002/0002362 | A1 * | 1/2002 | Humayun | A61F 9/0017 604/521 |
| 2004/0073231 | A1 * | 4/2004 | Juan, Jr. | A61F 9/00727 606/108 |
| 2005/0171507 | A1 * | 8/2005 | Christian | A61F 9/00781 604/524 |
| 2006/0149194 | A1 * | 7/2006 | Conston | A61F 9/00763 604/294 |
| 2006/0155300 | A1 * | 7/2006 | Stamper | A61F 9/00781 606/107 |
| 2007/0202186 | A1 * | 8/2007 | Yamamoto | A61K 9/0048 424/490 |
| 2010/0081988 | A1 * | 4/2010 | Kahle | A61B 17/3474 604/26 |
| 2010/0173866 | A1 * | 7/2010 | Hee | A61P 27/02 606/4 |
| 2012/0022424 | A1 | 1/2012 | Yamamoto | |
| 2012/0165851 | A1 * | 6/2012 | Murakami | B24B 21/004 606/185 |
| 2013/0253528 | A1 * | 9/2013 | Haffner | A61F 2/14 606/107 |
| 2014/0378960 | A1 * | 12/2014 | Fischer | A61B 5/0084 606/34 |
| 2016/0081712 | A1 * | 3/2016 | Heniford | A61B 5/0066 600/424 |
| 2018/0092633 | A1 * | 4/2018 | Peliks | A61B 10/0266 |
| 2021/0128356 | A1 * | 5/2021 | Moreno | A61F 9/00781 |

OTHER PUBLICATIONS

M. Dalton, "Can Schlemm's canal surgery be glaucoma's Holy Grail?", Opthamology Times, Apr. 17, 2015.

* cited by examiner

SECTION A - A

View B

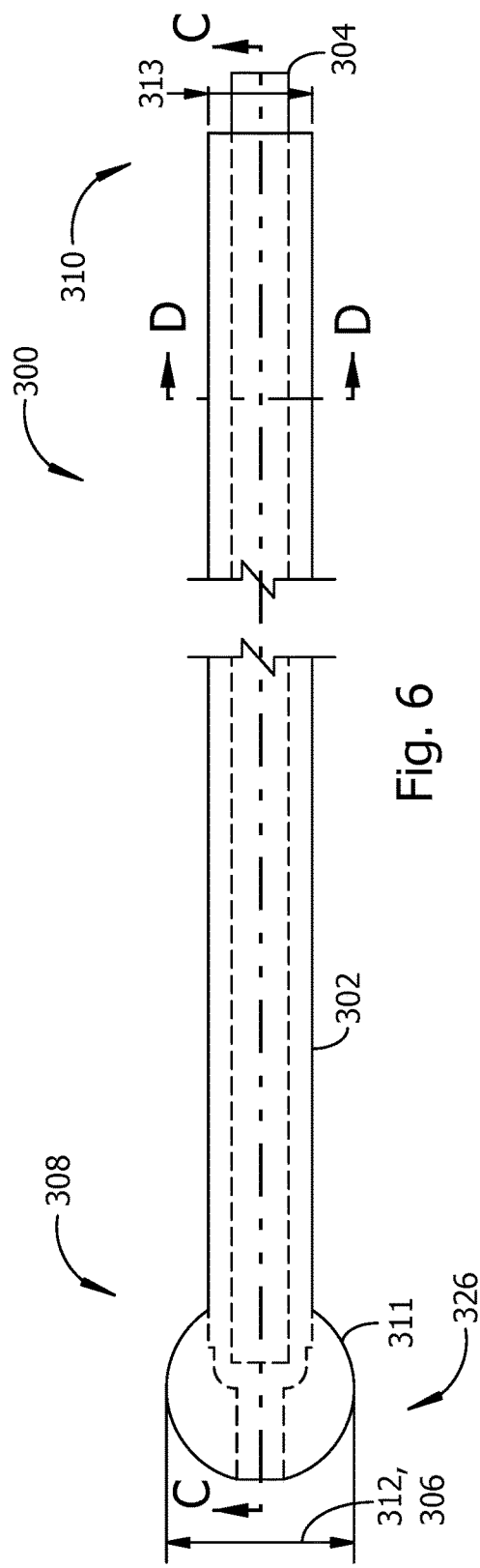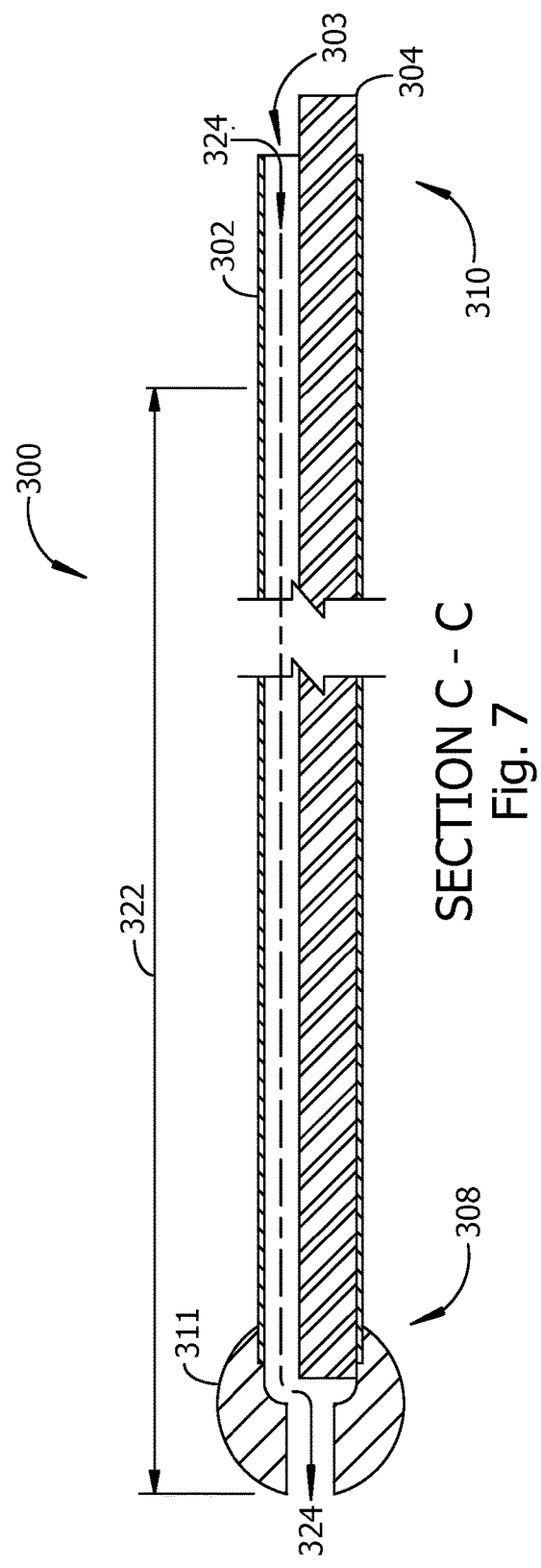

SECTION D - D

ALTERNATIVE SECTION D - D

ALTERNATIVE SECTION D - D

ALTERNATIVE SECTION D - D

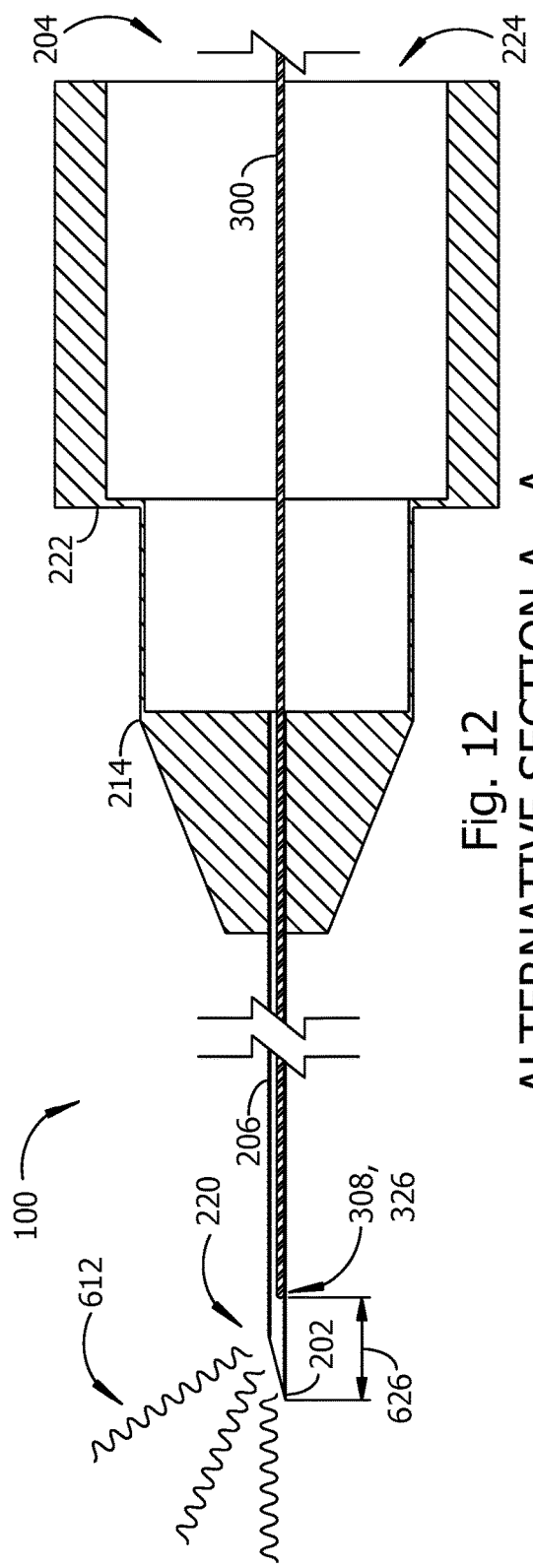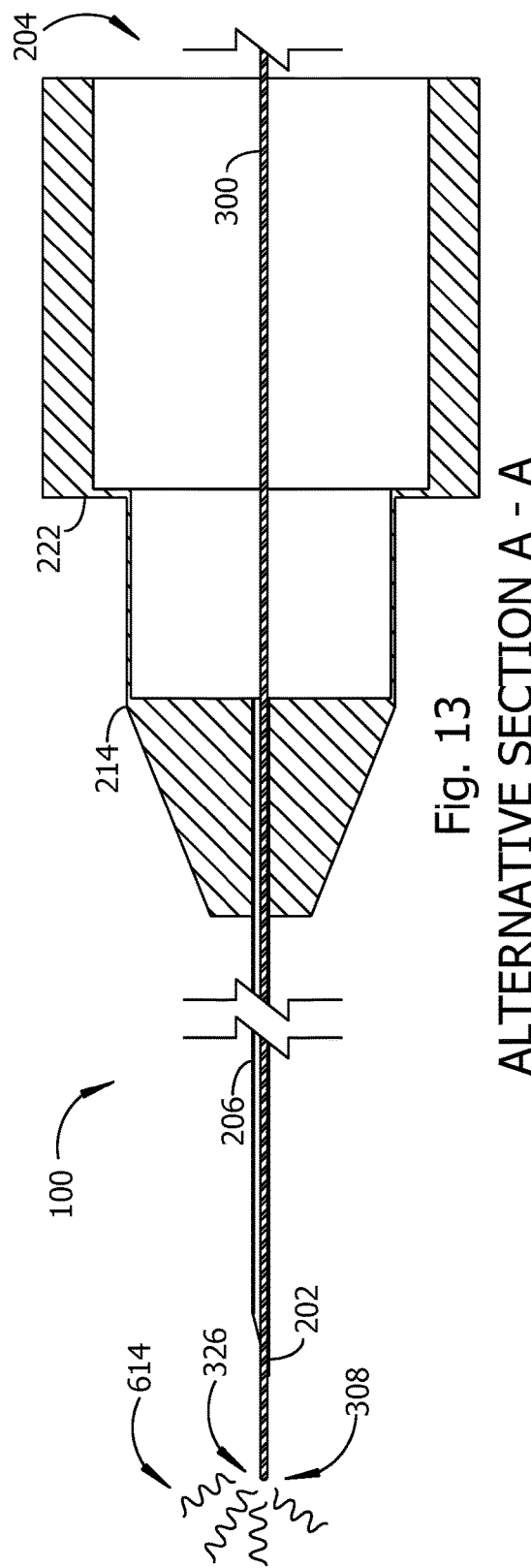

ALTERNATIVE
SECTION D - D

ALTERNATIVE
SECTION D - D

ALTERNATIVE
SECTION D - D

ALTERNATIVE
SECTION D - D

SECTION E - E

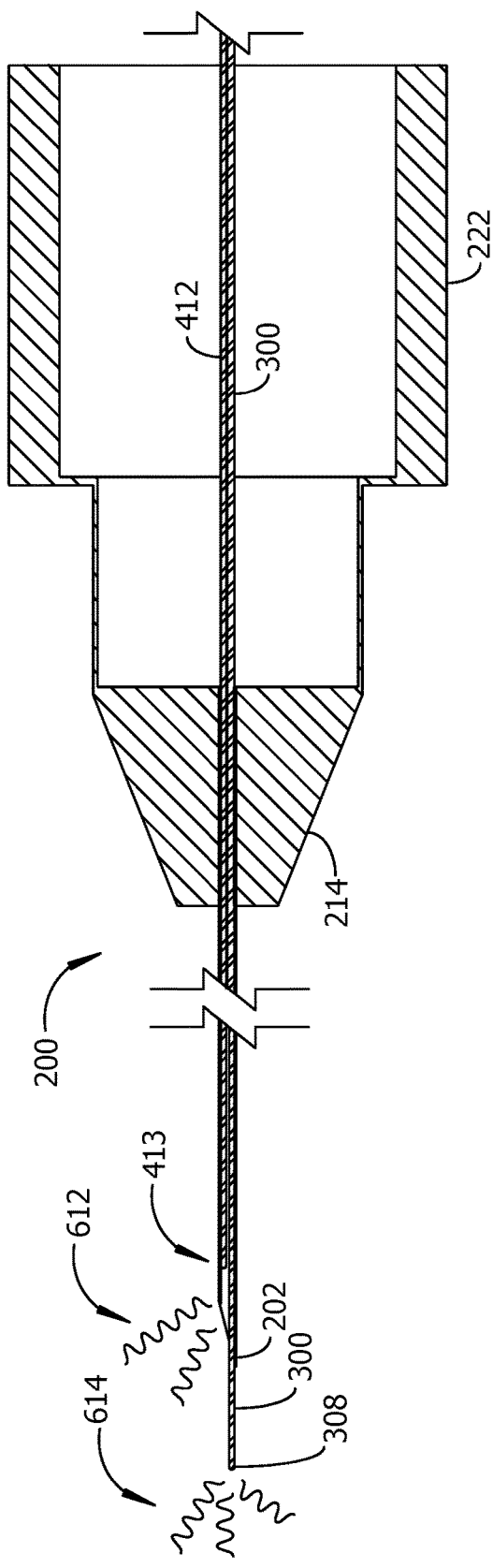
Fig. 23 ALTERNATIVE SECTION A - A
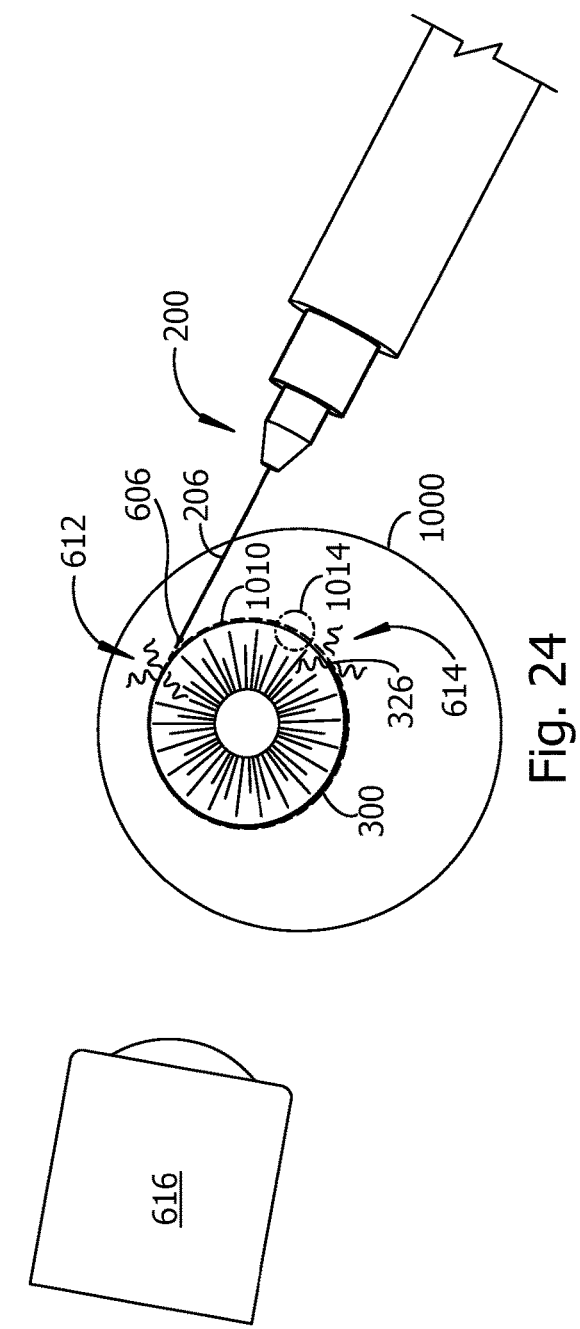
Fig. 24

ALTERNATIVE SECTION D - D

SECTION F - F

SECTION G - G

OPTHALMIC MICROSURGICAL INSTRUMENT

CROSS REFERENCE TO RELATED APPLICATIONS

This application is a continuation-in-part of copending application Ser. No. 15/892,833 filed Feb. 9, 2018, incorporated herein by reference in its entirety, which claims the benefit of U.S. Provisional Patent Application No. 62/574,136, filed Oct. 18, 2017, incorporated herein by reference in its entirety.

FIELD OF THE INVENTION

Embodiments are related to surgical apparatus for treatment of eye diseases such as glaucoma.

BACKGROUND

Aqueous humor is a transparent, watery fluid produced within an eye, filling the anterior and posterior chambers of the eye, transporting agents needed by eye tissues and helping to maintain the eye's rounded shape by fluid pressure. Aqueous humor flows out of the eye through a fluid drainage network including the trabecular meshwork and Schlemm's canal, a porous, circumferential fluid passage coupled to collector channels and veins. Blockage or collapse of parts of the eye's drainage network can lead to an increase in intraocular pressure, a condition that may be associated with degraded vision and eye diseases such as glaucoma.

Surgical treatment may be used to reduce intraocular pressure by improving the flow of aqueous humor. Some surgical treatments involve making relatively large incisions through the sclera, the tough white outer covering of the eye, forming a flap of tissue folded back to expose the trabecular meshwork or other parts of the flow path for aqueous humor. Exposed parts of the drainage network may then be modified by removing tissue or forming new drainage channels. An incision through the sclera may lead to a loss of fluid pressure inside the eye and a collapse of one or more of the chambers. It may be necessary to support the eye's natural shape by injecting a viscoelastic fluid into one of the chambers. A viscoelastic fluid has a viscosity that changes from dynamic to static flow conditions, flowing with relatively low viscosity when subjected to shear stress and assuming a gel-like, high-viscosity state under static conditions.

Surgical treatments involving incisions into the eye may increase the risk of post-surgical complications such as infection and the formation of scar tissue. Other treatment procedures less disruptive to the eye have been developed. For example, the flow of aqueous humor may be improved by passing a microcannula through parts of the eye's drainage network to remove obstructions or re-open collapsed fluid passages. Additionally, it can be advantageous to deliver drugs or drug-eluting devices or materials into tissue structures. Notably, the delivery of drugs and drug-eluting devices to Schlemm's Canal can be beneficial due to Schlemm's canal being outside the immune privileged area that is found inside the main body of the human eye. The microcannula may include a flexible hollow tube having an outer diameter small enough to permit the microcannula to be introduced into Schlemm's canal or some other part of the eye's drainage network. The microcannula may be sufficiently flexible to follow the curve of Schlemm's canal or another part of the drainage network while the microcannula is pushed from outside the eye, for example through a surgically-formed flap as previously described or through a puncture of the sclera. The microcannula may be used to mechanically expand a selected part of the drainage channel in the eye, or may be used to inject materials, objects, fluids, drugs, or viscoelastic to apply fluid pressure for improving flow through part of the eye's drainage system. Or, a microsurgical cutting, penetrating, or grasping instrument may be passed through the microcannula to guide the instrument to a part of the eye to be surgically modified.

Some microsurgical instruments have a microcannula slidably engaged with a hollow, flexible outer sheath. The flexible outer sheath may be used to position an entry point for the microcannula into the interior of an eye, with the microcannula passing through a lumen in the flexible outer sheath and the outer sheath held stationary with respect to the eye. An end of the microcannula may be extended from an end of the sheath to enter a selected part of an eye. However, the flexibility of the outer sheath may make it difficult for the sheath to penetrate the sclera or other tissue to enable the microcannula to enter drainage structures or other treatment areas inside the eye. It may be necessary to make an incision or puncture with a separate instrument to permit the flexible sheath to be positioned accurately for placement and guidance of the microcannula. Or, the microcannula may be provided with a tip shaped for tissue penetration, possibly limiting the use of the microcannula for delivering a payload into the interior of an eye.

SUMMARY

An example apparatus embodiment includes a trocar and a composite microcannula. An example of a trocar includes a rigid shaft having a proximal end and a distal end. The rigid shaft may be formed with a lumen extending from the proximal end to the distal end. The distal end of the rigid shaft on the trocar may be shaped for tissue penetration.

A composite microcannula may be positioned in the lumen of the trocar. An example of the composite microcannula may include a flexible hollow tube having an outer diameter less than an inner diameter of the lumen in the trocar. The example of a composite microcannula may further include a light guide.

Another example apparatus embodiment includes a trocar for ophthalmic surgery. The example of a trocar includes a rigid hollow shaft having a distal end shaped for tissue penetration. The hollow shaft is formed with a lumen extending from a distal end of the hollow shaft to a proximal end of the hollow shaft. The example of a trocar further includes a transition structure attached to the proximal end of the hollow shaft. The transition structure may be formed with an aperture for admitting a composite microcannula into the lumen. The example of a trocar may further include a light source disposed to illuminate the distal end of the rigid hollow shaft. A distal edge of the lumen in the hollow shaft may be smoothed to reduce abrasion and/or cutting of a solid object passing through the lumen and out of the trocar. The example of a trocar may further include a finger grip extending outward from the transition structure.

An example method embodiment includes placing a distal end of a composite microcannula within a lumen of a trocar; illuminating the distal end of the composite microcannula, thereby illuminating the distal end of the trocar; selecting a trocar entry point on an eye and positioning the trocar at the selected entry point; advancing the trocar at the selected entry point until the illuminated distal end of the trocar is observed to enter a selected structure in the eye; and extending the composite microcannula from the distal end of the trocar toward a target region in the eye, thereby transitioning from illuminating the distal end of the trocar to illuminating tissue outside the trocar.

BRIEF DESCRIPTION OF THE DRAWINGS

FIG. 6 is a partial top view of an example of a composite microcannula in accord with the embodiments of the microsurgical instrument.

FIG. 7 is a cross-sectional view C-C of the example composite microcannula of FIG. 6. The position and viewing direction for cross-sectional view C-C in FIG. 7 is marked with a longitudinal section line C-C in FIG. 6.

FIG. 12 is an alternative cross-sectional view A-A of another example of a trocar, further illustrating an example of a composite microcannula offset in a proximal direction from the distal end of the trocar, and further illustrating an example of an illuminated distal end of the trocar.

FIG. 13 continues the example of FIG. 12, showing an example of the illuminated distal end of the composite microcannula extending outward from the distal end of the lumen in the trocar.

FIG. 23 is another alternative cross-sectional view A-A of the example of a trocar of FIG. 1, showing an example of a composite microcannula with its light guide passing through the lumen of the trocar, and further showing positioned in the lumen a second, optional light guide separate from the light guide in the composite microcannula.

FIG. 24 shows a partial pictorial view of the example of a trocar with a composite microcannula and a second light guide as in the example of FIG. 23, illustrating an example of the illuminated distal ends of the trocar and composite microcannula separated from one another along the circumferential path of Schlemm's canal.

DESCRIPTION

Figure 1:
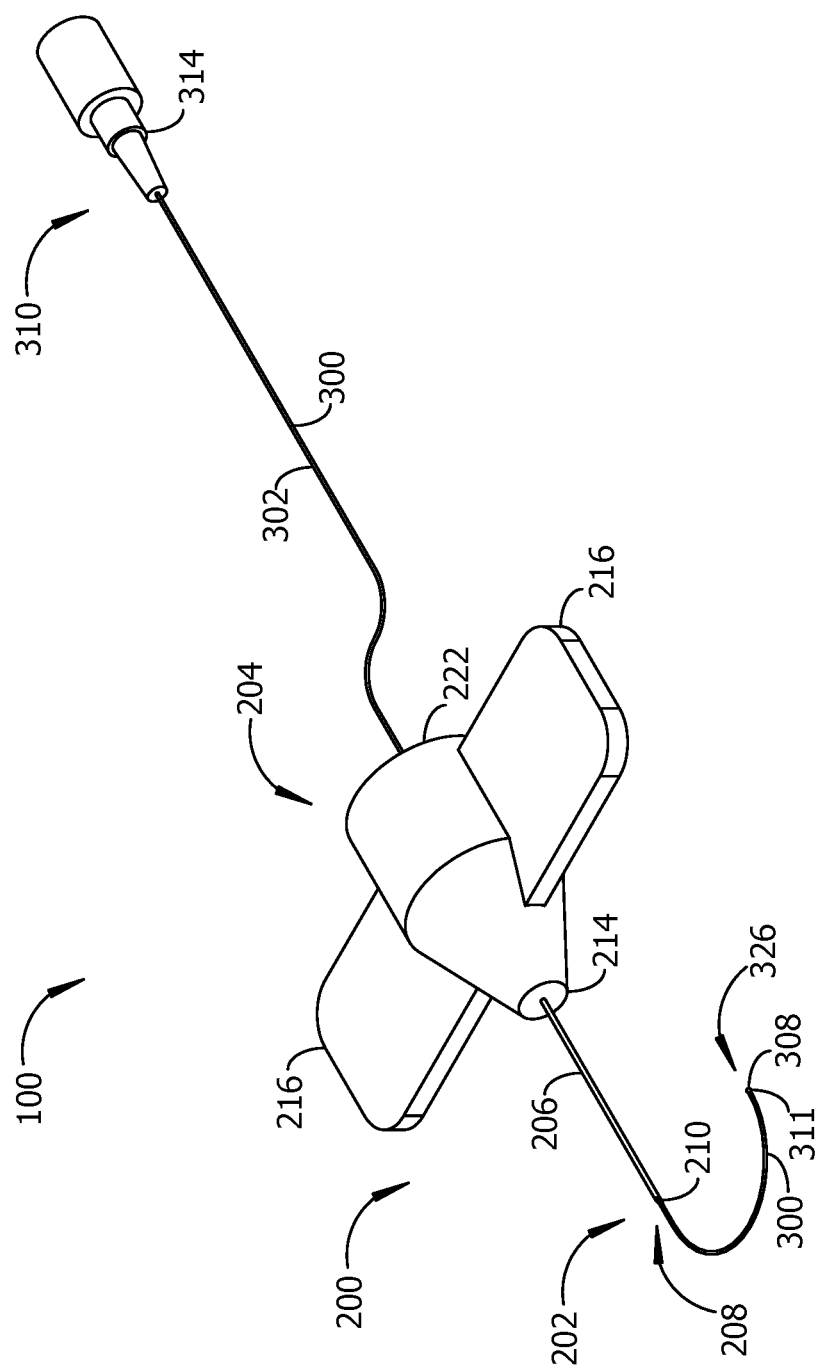
FIG. 1 is a pictorial view of an example embodiment of a microsurgical instrument including a trocar with a rigid hollow shaft and a flexible composite microcannula.

Example embodiments in accord with the invention are described herein. A trocar having a rigid hollow shaft with a distal end shaped for tissue penetration is configured to pierce biological tissue, for example the sclera of an eye, forming a very small entry point into the tissue for a composite microcannula passing through a lumen of the trocar. The composite microcannula, which may also be referred to herein as a composite microcatheter, includes a light guide for illuminating the distal end of the microcannula. A light source may be coupled to the composite microcannula and/or trocar to illuminate the distal end of the rigid hollow shaft by directing light through the light guide into the lumen of the trocar, thereby enabling an accurate determination of the position of the distal end of the trocar, a visual indication of the entry of the trocar a structure in the eye, and a visual indication of the position of the distal end of the composite microcannula as it advances toward a target region for treatment. The illuminated distal end of the composite microcannula may be used to determine when the microcannula has deviated from a preferred path, for example leaving a preferred path through Schlemm's canal and entering another channel or chamber such as a collector channel or another part of the eye's drainage system.

Embodiments are effective for providing a visual indication of the location of the distal end of the trocar by observing light emitted from the trocar through tissue which may include the sclera, trabecular meshwork or other tissue, including tissue not associated with an eye. Light passing through the sclera or other tissue from the trocar further indicates a direction of travel of the trocar. The position and direction of travel of the composite microcannula may also be accurately determined by visual observation of the light emitted from the tip of the microcannula. An embodiment may be accurately guided into tissues and/or tissue spaces such as, but not limited to, the trabecular meshwork, Schlemm's canal, and collector channels. Conversely, an embodiment may be accurately guided to specifically avoid entering a selected tissue or tissue space. The tissues in the eye and the position and direction of travel of an embodiment may be observed directly, with a camera, with a gonioprism, with other optical aids, or any combination of these devices and methods.

In some embodiments, a second light guide enables independent, and optionally simultaneous, illumination of the distal ends of the trocar and the composite microcannula. In other embodiments, a payload comprising a fluid and/or a solid object may be delivered through the composite microcannula to a target region in an eye. Examples of a fluid payload include, but are not limited to, drugs including gene therapy, stem cell, and other fluid-based drugs, a viscoelastic fluid, water, and a saline solution. Examples of a solid payload include, but are not limited to, devices, particles, nano particles, small devices including drug-eluting examples of solid payloads, a microsurgery instrument such as forceps, an instrument for penetrating and/or cutting tissue, a stent, a light guide, and a wire. As used herein, a light guide refers to an optical element capable of transmitting electromagnetic energy received at an input surface to an output surface through an intervening optical medium. Examples of a light guide include, but are not limited to, one or more mirrors arranged to direct a light beam from a source to a destination, a flexible optical fiber, a bundle of optical fibers, and a rigid light pipe.

Some embodiments include a positioner for displacing the composite microcannula relative to the distal end of the trocar. A positioner may optionally include a microcannula displacement mechanism configured to extend and optionally retract the composite microcannula. The positioner may further optionally include a fluid injector configured to move fluid from a fluid reservoir into the composite microcannula and possibly into a selected target region in an eye. Some embodiments of a positioner include a light source disposed to emit light into the light guide of the composite microcannula and optionally into a second light guide coupled to the trocar, when a second light guide is provided. A positioner may enable accurate advancement and/or retraction of the composite microcannula without disturbing the microcannula's entry point into the eye, possibly reducing an amount of time needed to complete a treatment procedure and reducing a risk of damage to eye tissue.

Embodiments of an ophthalmic microsurgical instrument may be configured to smoothly and continuously transition from illuminating the distal end of the trocar to illuminating tissue outside the trocar, thereby enabling very precise determination of the position of the trocar and composite microcannula relative to structures in the eye. The very small puncture made by the trocar in the sclera or other parts of the eye contrasts with the relatively large incisions required by previous surgical techniques that raise a flap of tissue from the sclera to access structures in the interior of the eye. The small puncture reduces patient discomfort and risk of post-operative complications such as scarring and infection. Preparing, monitoring and closing the surgical area are faster and less complicated than methods using incisions through the sclera, possibly enabling embodiments to be employed with less stringent levels of sterility and patient monitoring than may be practiced in an operating room for surgical procedures, and possibly permitting more rapid patient recovery and healing from surgical procedures.

An example embodiment of a microsurgical instrument appears in FIG. 1. The example embodiment 100 includes a trocar 200 configured to receive a composite microcannula 300. The composite microcannula 300 may be slidably engaged with the trocar 200, passing through a trocar connector 222 at the proximal end 204 of the trocar, a transition structure 214, and a lumen 208 formed in a rigid hollow shaft 206 extending outward from the transition structure 214 to the distal end 202 of the trocar 200. The rigid hollow shaft 206 is preferably formed with a distal end 210 shaped for tissue penetration. One or more of an optional finger grip 216 may be attached to, or alternately formed as an integral part of, the trocar connector 222 and/or the transition structure 214.

In the example of FIG. 1, the composite microcannula 300 is shown with several bends and curves to illustrate the flexibility of the hollow tube 302 forming much of the length of the composite microcannula. The flexibility of the composite microcannula enables the microcannula to follow the curved walls of a structure in the eye, for example Schlemm's canal, without puncturing or damaging the walls of the structure. An embodiment of the composite microcannula 300 may be formed with segments of the microcannula having flexural rigidity in a range from $3.0 \times 10^{-11}$ kN–m$^2$ to $2.9 \times 10^{-10}$ kN–m$^2$. Parts of the composite microcannula near the distal and/or proximal ends may optionally be more rigid than other parts of the composite microcannula. The rigid hollow shaft 206 of the trocar 200 is substantially stiffer than the composite microcannula and is preferably formed with a flexural rigidity of at least $1.5 \times 10^{-8}$ kN–m$^2$, stiff enough to readily penetrate the sclera and other tissue in an eye. A trocar with flexural rigidity greater than the preferred minimum value may eliminate the need for a separate surgical instrument to form a puncture through an outer surface of an eye.

The composite microcannula 300 may include an optional microcannula connector 314 at the proximal end 310 of the flexible hollow tube 302. The microcannula connector may include connections for introducing a payload into the composite microcannula and for coupling light from a light source into the composite microcannula. A liquid, solid, or gaseous payload introduced into the proximal end 310 may be transported through the hollow tube 302 to the distal end 308 of the composite microcannula for delivery to a target region in an eye. Light incident on the proximal end 310 may travel to the distal end 308 to create an illuminated distal end 326 of the composite microcannula. An optional light diffuser 311 may be provided at the distal end 308 to disperse light in many directions, thereby indicating the precise location of the distal end of the composite microcannula as it moves through channels and chambers in an eye. Light may travel from the proximal end to the distal end of the composite microcannula by internal reflection from the walls of the flexible hollow tube 302, through a liquid introduced into the hollow tube 302, or through one or more light guides included with some embodiments of a composite microcannula.

Figure 2:
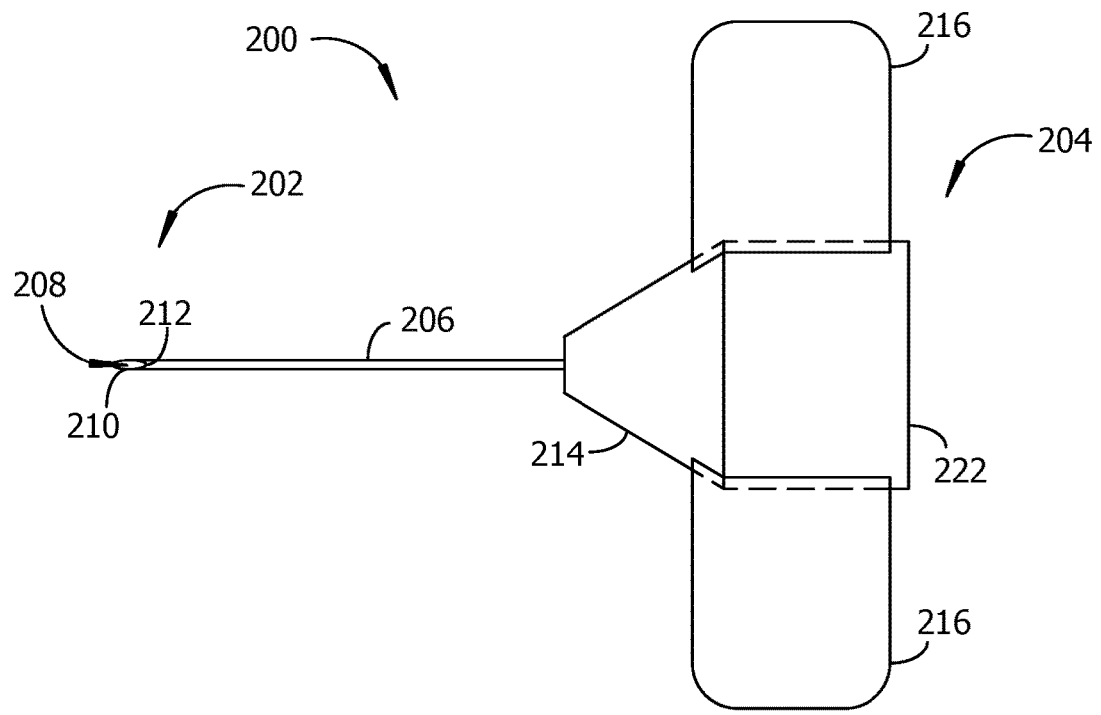
FIG. 2 is a top view of an example of a trocar in accord with an embodiment.
Figure 3:
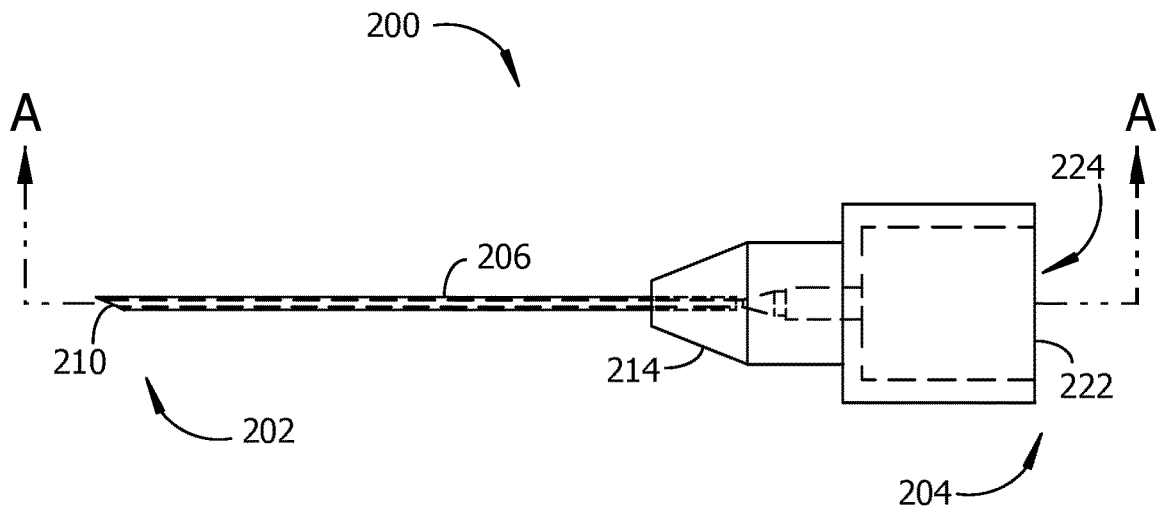
FIG. 3 is a side view of the example of a trocar of FIG. 2.

An example embodiment of a trocar 200 is shown in a top view in FIG. 2 and a side view in FIG. 3. In the example of FIG. 3, the optional finger grips 216 visible in FIG. 2 have been omitted. The trocar connector 222 at the proximal end 204 of the trocar 200 may be a luer connector, for example a slip-fit or twist-lock luer connector. Other connectors capable of forming a leak-resistant seal may alternatively be used. The rigid hollow shaft 206 of the trocar 200 attaches to the transition structure 214. A lumen 208 in the rigid hollow shaft 206 is in fluid communication with void spaces in the transition structure and trocar connector, thereby enabling fluid to be introduced into the lumen 208. The lumen 208 of the trocar 200 extends through the distal end shaped for tissue penetration 210.

Figure 4:
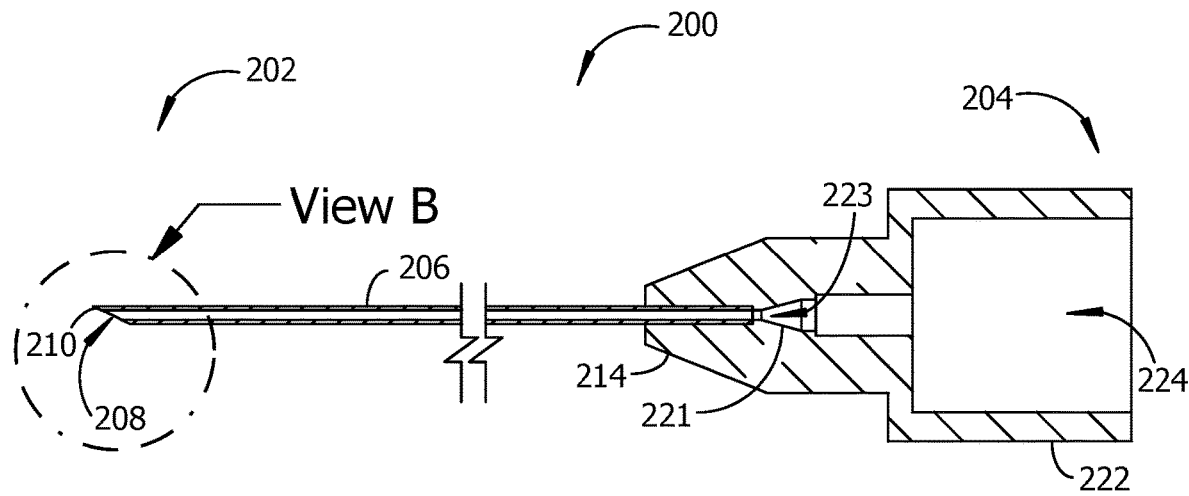
FIG. 4 is a cross-sectional view A-A of the example of a trocar of FIGS. 1-3. A section line labelled A-A in FIG. 3 shows the position and viewing direction for the cross-sectional view in FIG. 4.
Figure 5:
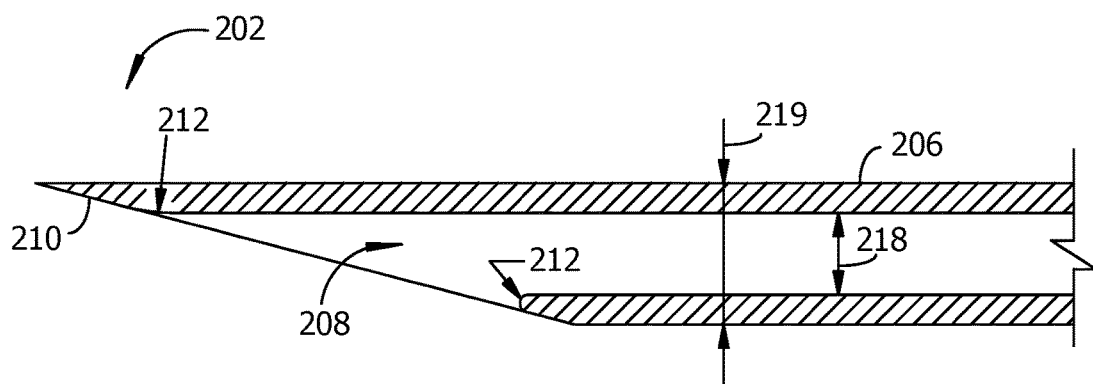
FIG. 5 is an enlarged partial cross-sectional view B of the rigid hollow shaft of FIGS. 1-4, showing an example of a distal end shaped for tissue penetration and further showing an example of a smoothed distal edge of the lumen in the trocar. The position of View B in FIG. 5 is marked with a broken line in FIG. 4.

Cross-sectional view A-A in FIG. 4 and partial enlarged view B in FIG. 5 illustrate some internal details of an example of a trocar 200 in accord with an embodiment. The rigid hollow shaft 206 is held firmly by the transition structure 214 attached to the trocar connector 222. The lumen 208 through the rigid hollow shaft 206 is in fluid communication with void spaces 224 in the trocar connector 222. The void space 224 may be formed with a conical microcannula guide surface 221 near the proximal end of the hollow shaft 206. The conical surface 221 may deflect a composite microcannula toward the lumen 208 through an aperture 223 formed in the transition structure 214 near the distal end of the void space 224.

The distal edge 212 of the lumen 208 is preferably smoothed, for example by rounding the edge 212 all the way around the distal end of the lumen. The smoothed distal edge 212 reduces abrasion or cutting of material from the composite microcannula when the microcannula slides across the distal edge of the trocar lumen. If left unsmoothed, the distal edge of the trocar lumen may be sharp enough to remove material from the composite microcannula. Reducing an amount of material cut or abraded from the composite microcannula reduces undesirable deposition of such material in an eye.

View B in FIG. 5 further illustrates an example of an outer diameter 219 of the rigid hollow shaft 206 and an inner diameter 218 of the lumen 208 through the rigid hollow shaft 206. The outer diameter 219 may be in a range from about 200 microns to about 700 microns. For example, some trocar embodiments have a rigid hollow shaft with an outer diameter 219 of 450 microns. Other trocar embodiments have a rigid hollow shaft with an outer diameter 219 of 250 microns. The inner diameter 218 is preferably larger than a largest transverse dimension 306 of a composite microcannula configured to pass slidably through the lumen, for example an outer diameter 306 of the flexible hollow tube 302, a largest transverse dimension 306 across the tube 302 and an outer coating 321 applied to the tube, a largest transverse 306 dimension across the hollow tube 302 and an external light guide 304 in contact with the tube, or an outer diameter 306 of a sleeve 320 surrounding the tube 302.

An example embodiment of a composite microcannula 300 is shown in a top view in FIG. 6, a longitudinal cross-sectional view C-C in FIG. 7, and alternative transverse cross-sectional views D-D in FIGS. 8-11. As suggested in FIGS. 6, 7, and 8, light guide 304 may be positioned in a longitudinal void 303 extending from the proximal end 310 to the distal end 308 of the flexible hollow tube 302. The longitudinal void 303 inside the composite microcannula 300 may also be referred to as the lumen 303 of the composite microcannula. The void 303 may serve as a fluid path 324 for a fluid introduced into the flexible hollow tube 302. A payload introduced onto the composite microcannula may follow the fluid path 324 as the payload moves from the proximal end 310 to the distal end 308.

Figure 31:
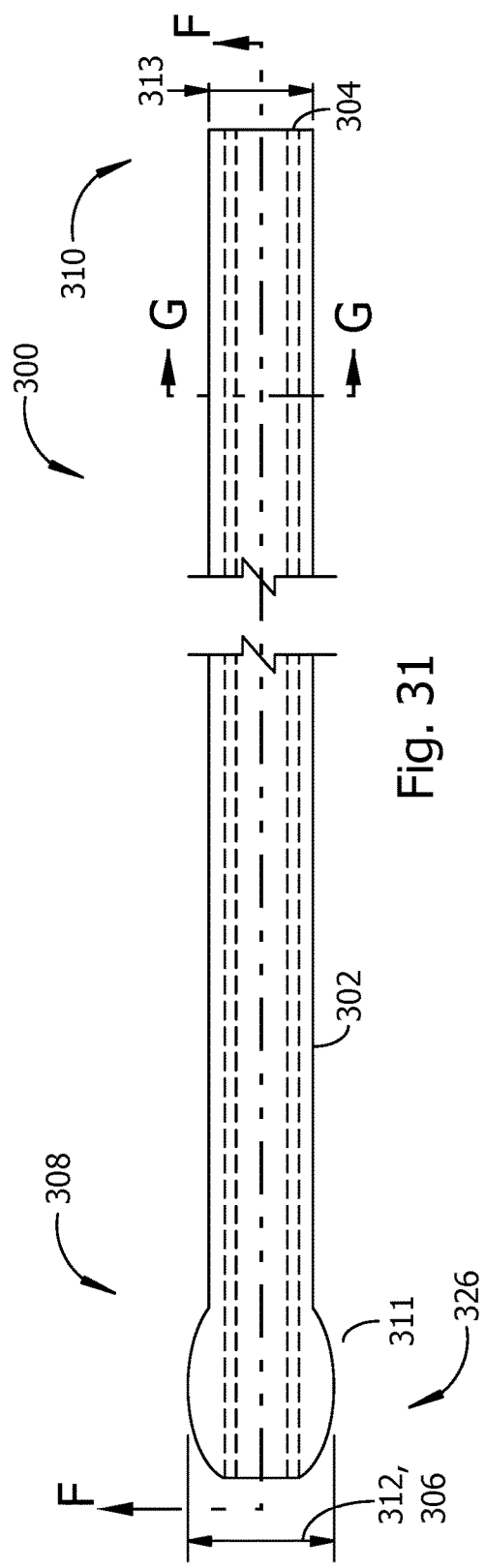
FIG. 31 is a partial top view of another example of a composite microcannula in accord with the embodiments of the microsurgical instrument.
Figure 32:
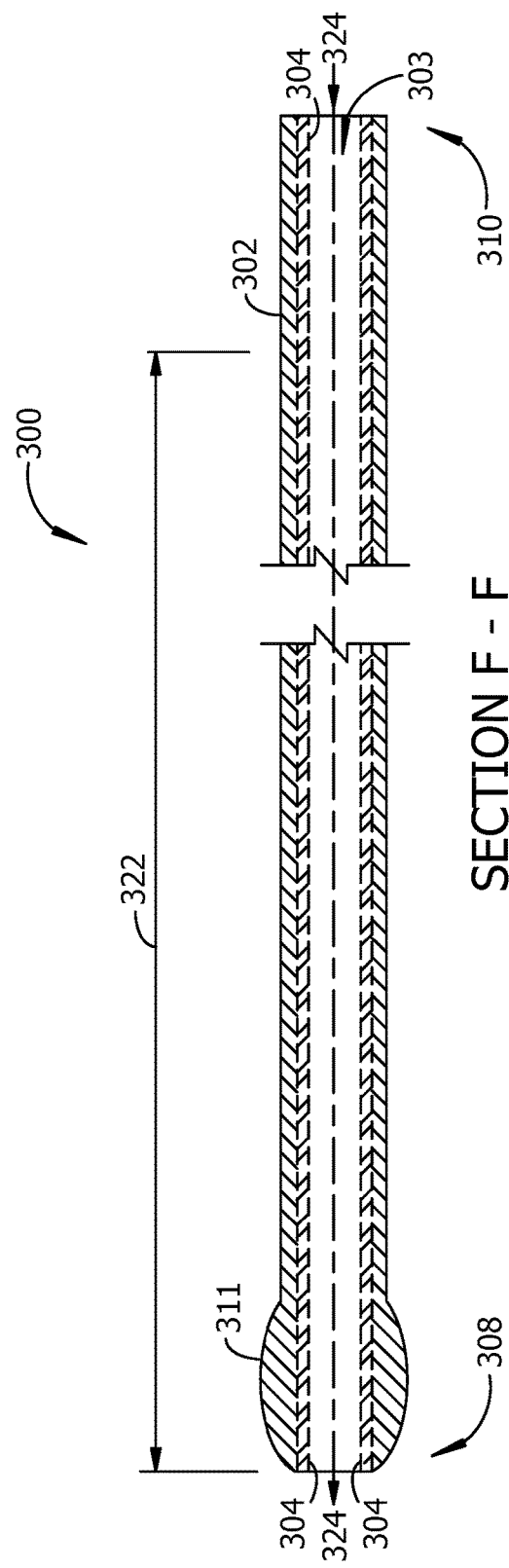
FIG. 32 is a cross-sectional view F-F of the example composite microcannula of FIG. 31. The position and viewing direction for cross-sectional view F-F in FIG. 32 is marked with a longitudinal section line F-F in FIG. 31.
Figure 33:
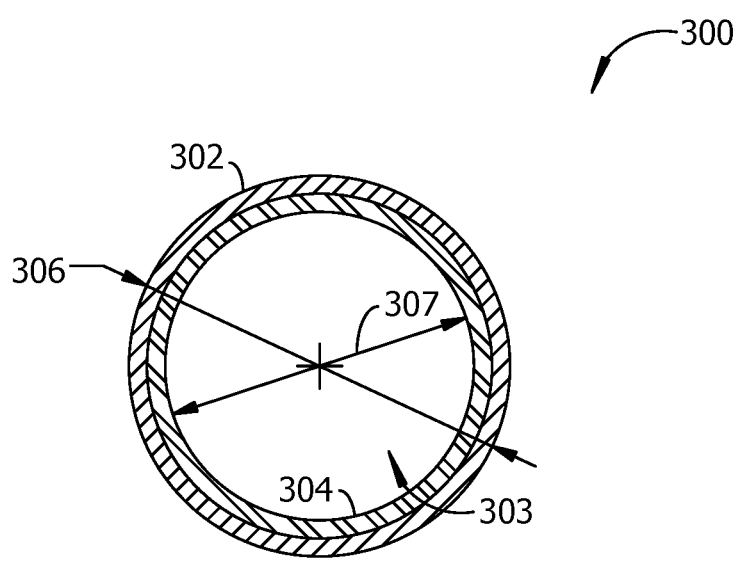
FIG. 33 is a cross-sectional view G-G of the example composite microcannula of FIGS. 30-31. The position and viewing direction for cross-sectional view G-G in FIG. 33 is marked with a transverse section line G-G in FIG. 31.

The light guide 304 may be formed separately from the flexible hollow tube as suggested in the previous examples. Alternatively, a light guide may be formed as an internal layer of the flexible hollow tube 302 as shown in the examples of FIGS. 31, 32, and 33. The light guide 304 may be disposed as a concentric layer of material adjacent the void 303 in the composite microcatheter 300. An index of refraction of the material of the light guide 304 preferably differs sufficiently from an index of refraction of the material of the flexible hollow tube 302 to enable efficient coupling of light from a light source to the distal end 308 by internal reflection through the light guide. The layer of material forming the light guide 304 may be formed by molding, chemical deposition, or by mechanically inserting a hollow tube into the flexible hollow tube 302. Although the figures show an example of a light guide made from a single layer of material, the light guide may alternatively be made of several layers of material, each with a selected value of refractive index, or may alternatively be made with a refractive index that varies with distance from an edge of the light guide.

FIGS. 31, 32, and 33 further illustrate an example of a light diffuser 311 having a reduced outside diameter 312 compared to the outside diameter of the light diffuser 311 in the examples of FIGS. 6 and 7. The light diffuser 311 may alternatively be formed as a rounded end of the flexible hollow tube 302, where the diffuser has a radius equal to half the diameter 313 of the flexible hollow tube.

A second light guide and/or other liquid or solid payloads may be passed through the void 303 surrounded by the light guide 304. In some embodiments, the light guide 304 entirely surrounds the void space 303 in the flexible hollow tube 302. Alternatively, the light guide may be not entirely surround the void space, for example being formed as a hollow tube split longitudinally in half, in quarter, or some other fraction of a complete hollow tube.

An outer diameter 306 of the composite microcannula 300 may be the largest diameter found on the composite microcannula, for example the diameter 312 in FIG. 6. The outer diameter 306, for example the larger of the outside diameter 312 of an optional light diffuser 311 at the distal end 308 and the outside diameter 313 of the hollow tube 302, is preferably less than the internal diameter 218 of the lumen 208 in the trocar 200.

The distal end 308 of the composite microcannula corresponds to the illuminated end 326 when light incident on the proximal end 310 of the light guide 304 is emitted from the distal end 308. As suggested in FIGS. 6 and 7, the distal end 308 of the composite microcannula may be rounded to reduce tissue trauma and to disperse light from the light diffuser 311 in many directions to enhance the visibility of the illuminated distal end 326. The outside diameter 312 of the light diffuser may be larger than the outside diameter 313 of the hollow tube 302. Alternately, the diameters (312, 313) may be approximately equal to one another.

For some embodiments, a length of a flexible segment 322 of the composite microcannula 300 may be a few millimeters longer than a circumferential length of Schlemm's canal. The circumferential length of Schlemm's canal in a human eye is about 36 millimeters. For some embodiments of a composite microcannula 300, the length of the flexible segment 322 may be greater than 40 millimeters (1.6 inches). A length of the flexible segment 322 may optionally be substantially longer than the circumferential length of Schlemm's canal, for example to permit the composite microcannula to connect to a light source or fluid injection apparatus or to provide a convenient length outside the proximal end of the trocar for gripping the composite microcannula with forceps or fingers.

Alternatively, the length of the flexible segment 322 of the composite microcannula 300 may be about 20 millimeters, allowing catheterization of Schlemm's canal in two passes. A first pass may proceed through about half of the length of Schlemm's canal in a clockwise direction. A second pass may proceed through the other half of Schlemm's canal in a counterclockwise direction.

Figure 8:
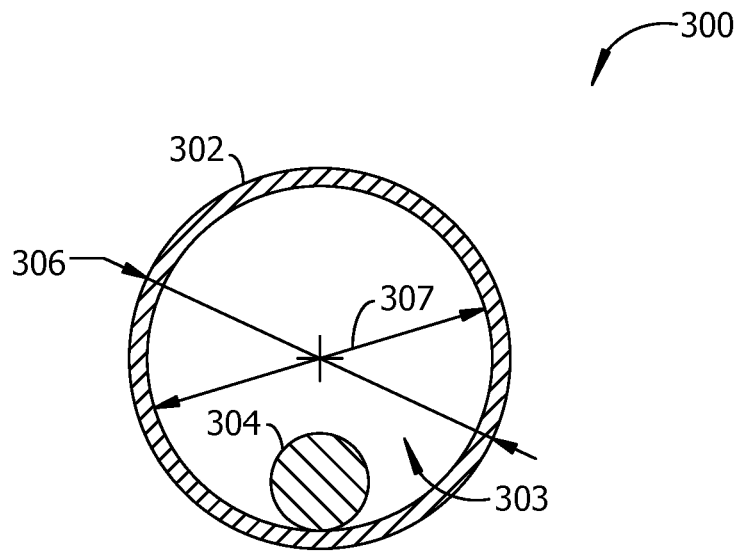
FIG. 8 is a cross-sectional view D-D of the example composite microcannula of FIG. 6. The position and viewing direction for cross-sectional view D-D in FIG. 8 is marked with a transverse section line D-D in FIG. 6.

In the example of a composite microcannula 300 in FIG. 8, the light guide 304 is positioned within the longitudinal void 303. The light guide has a smaller diameter than the inner diameter 307 of the flexible hollow tube 302. The outer diameter 306 of the composite microcannula 300 may be the outer diameter of the hollow tube 302.

Figure 9:
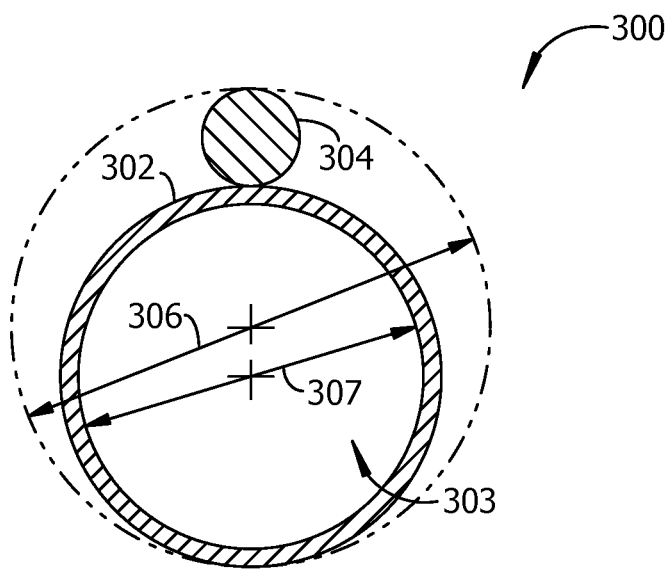
FIG. 9 is an alternative cross-sectional view D-D of another example of a composite microcannula in accord with embodiments of the microsurgical instrument. The position and viewing direction for alternative cross-sectional view D-D in FIG. 9 is marked with the transverse section line D-D in FIG. 6.

In the example of a composite microcannula 300 in FIG. 9, the light guide 304 is positioned on the outside surface of the flexible tube 302, leaving the space inside the flexible tube 302 available for transporting a payload through the composite microcannula. In the example of FIG. 9, the outer diameter 306 of the composite microcannula includes the dimensions of the flexible tube 302 and the light guide 304.

Figure 10:
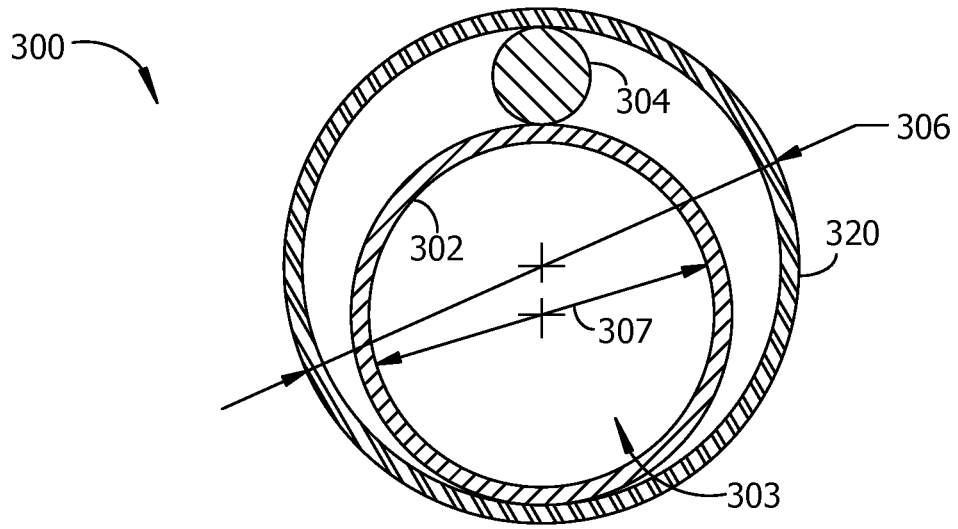
FIG. 10 is an alternative cross-sectional view D-D of another example of a composite microcannula in accord with embodiments of the microsurgical instrument. The position and viewing direction for alternative cross-sectional view D-D in FIG. 10 is marked with the transverse section line D-D in FIG. 6.
Figure 11:
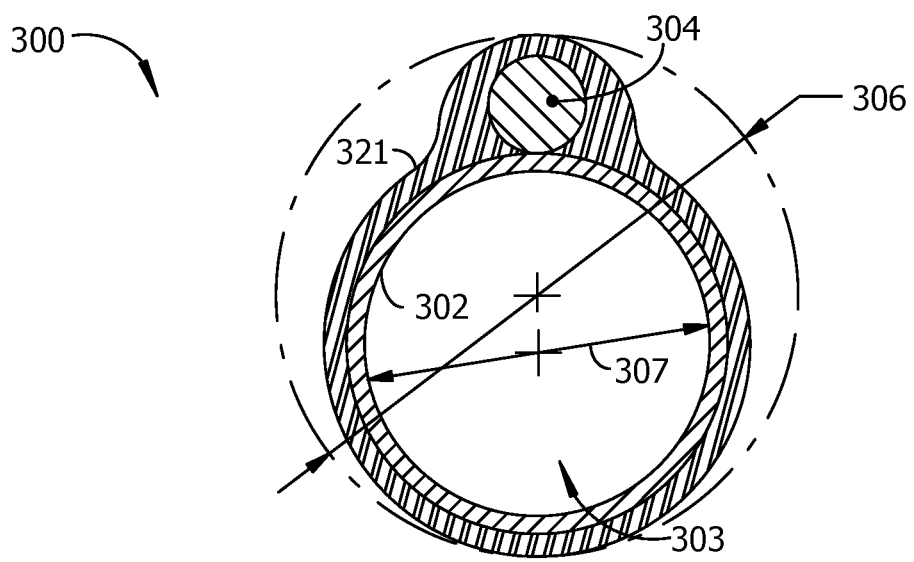
FIG. 11 is an alternative cross-sectional view D-D of another example of a composite microcannula in accord with embodiments of the microsurgical instrument. The position and viewing direction for alternative cross-sectional view D-D in FIG. 11 is marked with the transverse section line D-D in FIG. 6.
Figure 14:
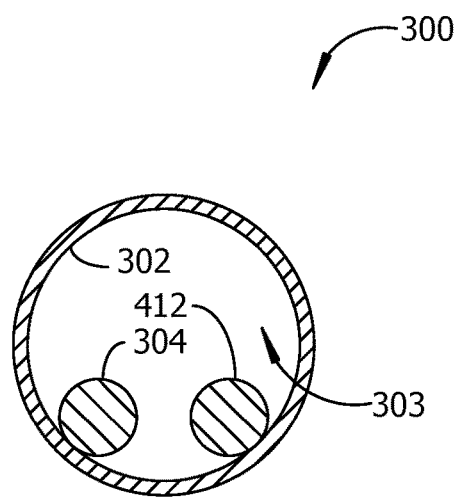
FIG. 14 is an alternative cross-sectional view D-D showing another example of a composite microcannula with two light guides in the interior longitudinal void of the composite microcannula's flexible hollow tube.

FIGS. 10 and 11 show more examples of a composite microcannula 300 in accord with a microsurgical instrument embodiment 100. The example composite microcannula 300 in FIG. 10 positions the light guide 304 outside the void 303 in the flexible hollow tube 302. An outer sleeve 320 surrounds the light guide 304 and the flexible tube 302. The outer diameter 306 of the composite microcannula may correspond to the outer diameter of the sleeve 320 in FIG. 10. In FIG. 11, an example of a coating 321 has been applied over the light guide 304 and flexible hollow tube 302. The outer diameter 306 along the flexible segment of the composite microcannula includes the dimensions of the hollow tube 302, light guide 304, and outer coating 321. The example embodiments in FIGS. 10 and 11 both offer the full internal diameter 307 of the hollow tube 302 for carrying a payload through the longitudinal void 303.

The composite microcannula may be positioned inside the lumen of the trocar to illuminate the distal end of the trocar while the trocar is being inserted into an eye. FIGS. 12 and 13 show an example of an alternative configuration for a transition structure 214 and examples of positions of the composite microcannula. In FIG. 12, the composite microcannula is positioned for lighting the distal end 202 of the trocar's rigid hollow shaft 206. The distal end 308 of the composite microcannula, which in the examples of FIGS. 12-13 is also the illuminated end 326 of the microcannula, may be installed in the lumen of the trocar a preferred offset distance 626 from the distal end 202 of the trocar. Internal reflection in the trocar lumen causes light 614 emitted from the distal end of the composite microcannula to emerge from the distal end of the trocar as light 612 dispersed across a wide range of angles, making the trocar tip visible from many different viewing directions. The illuminated distal end 220 of the trocar may be used to identify the precise location of the tip of the trocar inside eye tissue. For example, a readily perceived change in the brightness, as may be observed through the trabecular meshwork gonioscopically, of the emitted light 612 indicates when the distal end of the trocar has passed through the sclera and entered Schlemm's canal.

Advancing the illuminated distal end 326 of the composite microcannula out of the lumen in the trocar causes a smooth transition from illuminating the tip of the trocar to illuminating tissue outside the trocar. In the example of FIG. 13, light 614 emitted from the illuminated distal end 326 of the composite microcannula may be dispersed across a wide range of angles, accurately indicating the position of the tip of the composite microcannula inside an eye.

Figure 15:
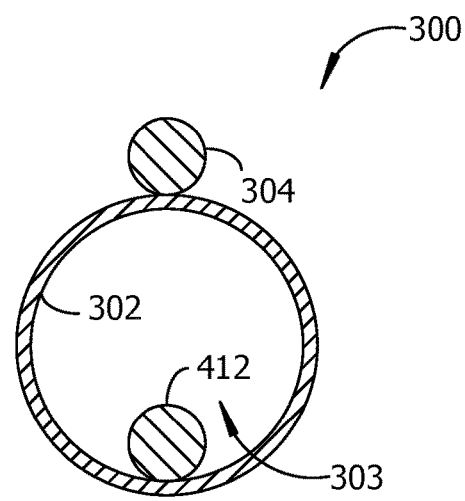
FIG. 15 is an alternative cross-sectional view D-D showing another example of a composite microcannula with two light guides, one light guide in the interior of the composite microcannula's flexible hollow tube, and another light guide contacting an external surface of the flexible hollow tube.
Figure 16:
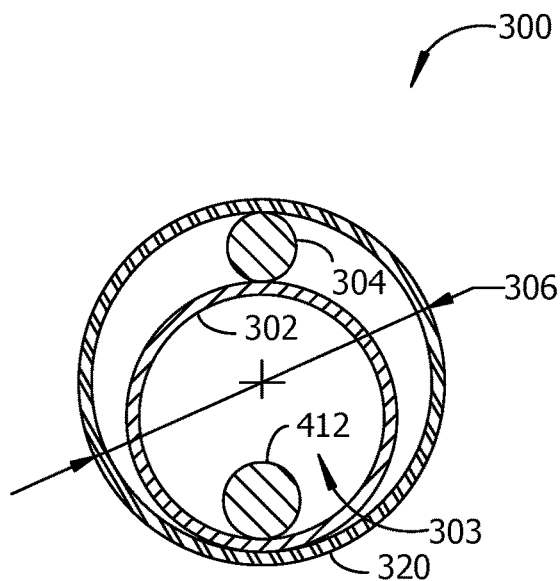
FIG. 16 is an alternative cross-sectional view D-D showing another example of a composite microcannula with two light guides, one light guide in the interior of the composite microcannula's flexible hollow tube, and another light guide between the hollow tube and an outer sleeve.
Figure 17:
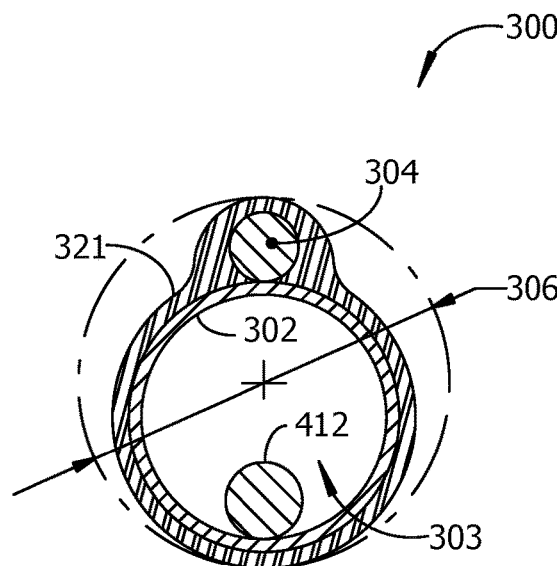
FIG. 17 is an alternative cross-sectional view D-D showing another example of a composite microcannula with two light guides, one light guide in the interior of the composite microcannula's flexible hollow tube, and a second light guide held against the flexible hollow tube by an outer coating applied over the second light guide and the flexible hollow tube.

Some alternative embodiments of a composite microcannula include two light guides as shown in the examples of FIGS. 14-17. In the example of a composite microcannula 300 in FIG. 14, a first light guide 304 and a second light guide 412 are disposed within the lumen 303 of the hollow tube 302. In the example of FIG. 15, the first light guide 304 may be outside the lumen 303 of the hollow tube 302, and the second light 412 may be inside. In the example of FIG. 16, both light guides may be positioned as in FIG. 15, with an outer sleeve 320 surrounding the flexible hollow tube 302 and the first light guide 304. In the example of FIG. 17, both light guides may again be positioned as in FIG. 15, but an outer coating 321 is applied over the first light guide 304 and flexible hollow tube 302.

Figure 18:
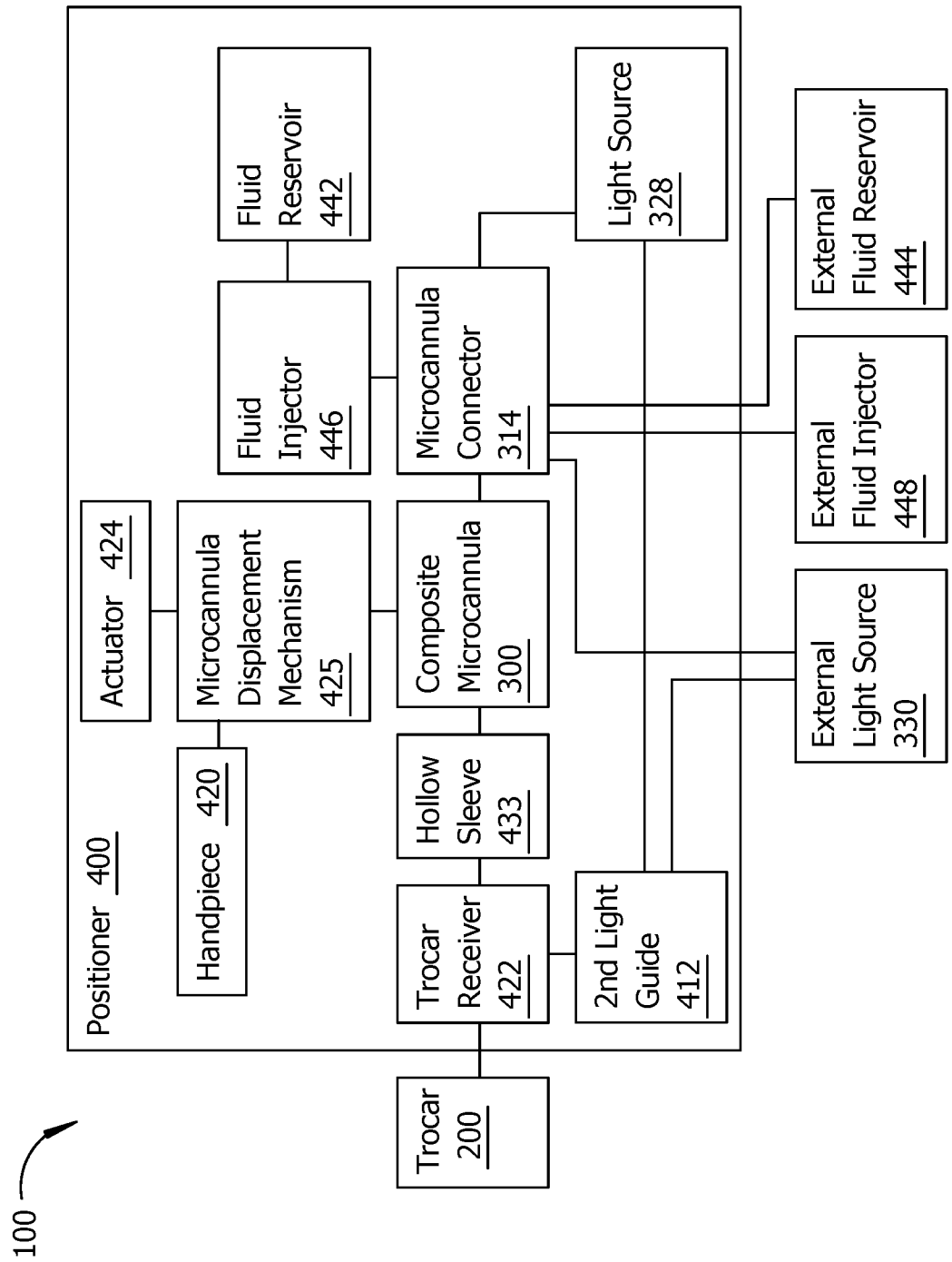
FIG. 18 is a block diagram of an alternative apparatus embodiment including a positioner for displacing the composite microcannula relative to the trocar, and optionally including a fluid injector for introducing fluid into the composite microcannula.

Some embodiments of a microsurgical instrument include a positioner for displacing the composite microcannula relative to the trocar. A block diagram of an alternative embodiment of a microsurgical instrument 100 with a positioner is shown in the example of FIG. 18. The positioner 400 may include a handpiece 420 holding a microcannula displacement mechanism 425 configured to extend, and optionally retract, the composite microcannula 300 from the trocar 200. The trocar 200 may be attached to a trocar receiver 422, for example a receiver for the luer fitting on the trocar. The composite microcannula may pass through a hollow sleeve 433 disposed between the trocar receiver 422 and the microcannula displacement mechanism 425. The hollow sleeve 433 may improve smooth extension and retraction of the composite microcannula by reducing buckling or kinking of the flexible part of the composite microcannula inside the positioner 400 when the microcannula displacement mechanism is operated. An actuator 424 mechanically linked to the microcannula displacement mechanism 425 enables manual control of the length of the composite microcannula extended from the distal end of the trocar.

An optional light source 328 may be provided inside the positioner 400. Light output from the light source 328 may be coupled into the microcannula connector 314 attached to the composite microcannula 300. The microcannula connector 314 may optionally be configured to receive light from an external light source 330. In some embodiments, the light source 328 may be disposed to transmit light through the second light guide 412 into the lumen of the trocar 200, possibly through the intervening trocar receiver 422.

The microcannula connector 314 may optionally provide a fluid connection to a fluid injector 446 disposed to transfer fluid from a fluid reservoir 442 inside the handpiece 420 to the composite microcannula 300. The microcannula connector 314 may alternatively be connected to an external fluid injector 448 configured to move fluid from an external fluid reservoir 444 into the composite microcannula 300.

Figure 19:
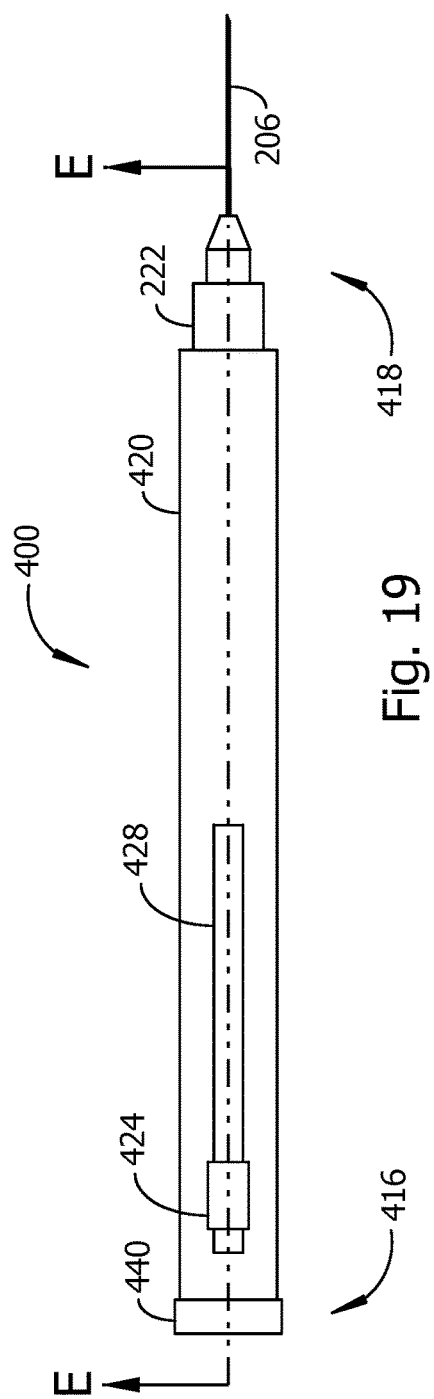
FIG. 19 shows a top view of an example of a microsurgical instrument embodiment with a positioner and a trocar.
Figure 20:
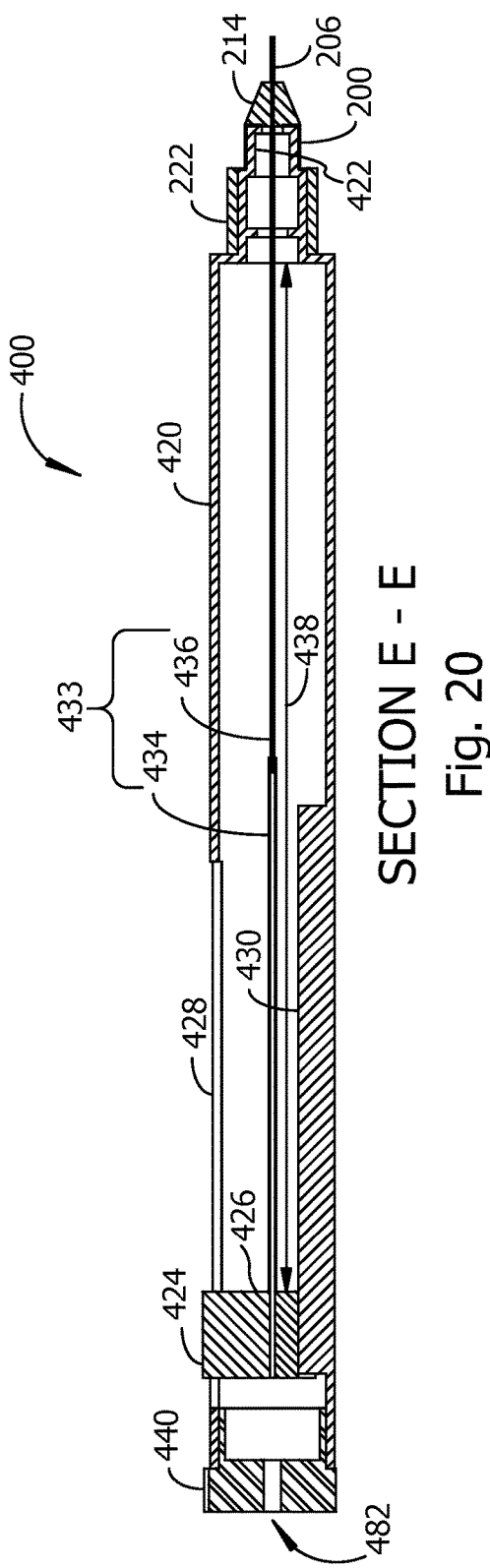
FIG. 20 is a cross-sectional view E-E of the example of a positioner from FIG. 19. A location and viewing direction for cross-sectional view E-E in FIG. 20 is marked with a longitudinal section line labeled E-E in FIG. 19.

FIGS. 19 and 20 show some details of an example of a microsurgical instrument embodiment 100 including a positioner 400. The trocar connector 222 at the proximal end of the trocar 200 connects to the trocar receiver 422 at the distal end 418 of the positioner 400. The trocar receiver 422 may be formed as an integral part of the handpiece 420, or may alternately be formed separately and strongly attached to the handpiece. An actuator 424 slidably engages with the handpiece 420 along an actuator aperture 428 to extend the composite microcannula from the trocar. The actuator may be attached to, or alternately formed as an integral part of, a guide block 426 configured to track along a guide ridge 430 inside the handpiece 420.

A hollow sleeve 433 may be connected at its proximal end to the guide block 426 and at its distal end to the trocar 200. A composite microcannula (not visible in FIGS. 19-20) may be positioned inside the hollow sleeve 433. The hollow sleeve may include a fixed segment 436 attached to, or alternately formed as an integral part of, the trocar 200, and a movable segment 434 connected to the actuator block 426, where the length 438 of the hollow sleeve 433 includes both the fixed and movable segments. The fixed and movable segments of the hollow sleeve 433 may alternately be implemented as a hollow, collapsible and extendable bellows sleeve with concertinaed sides. The length 438 of the hollow sleeve 433 may change with a displacement of the composite microcannula 300 relative to the trocar 200.

An end cap 440 may close off the proximal end 416 of the positioner 400. The end cap 440 may be formed with a cap aperture 482 to permit the composite microcannula to extend out from the proximal end 416.

Figure 21:
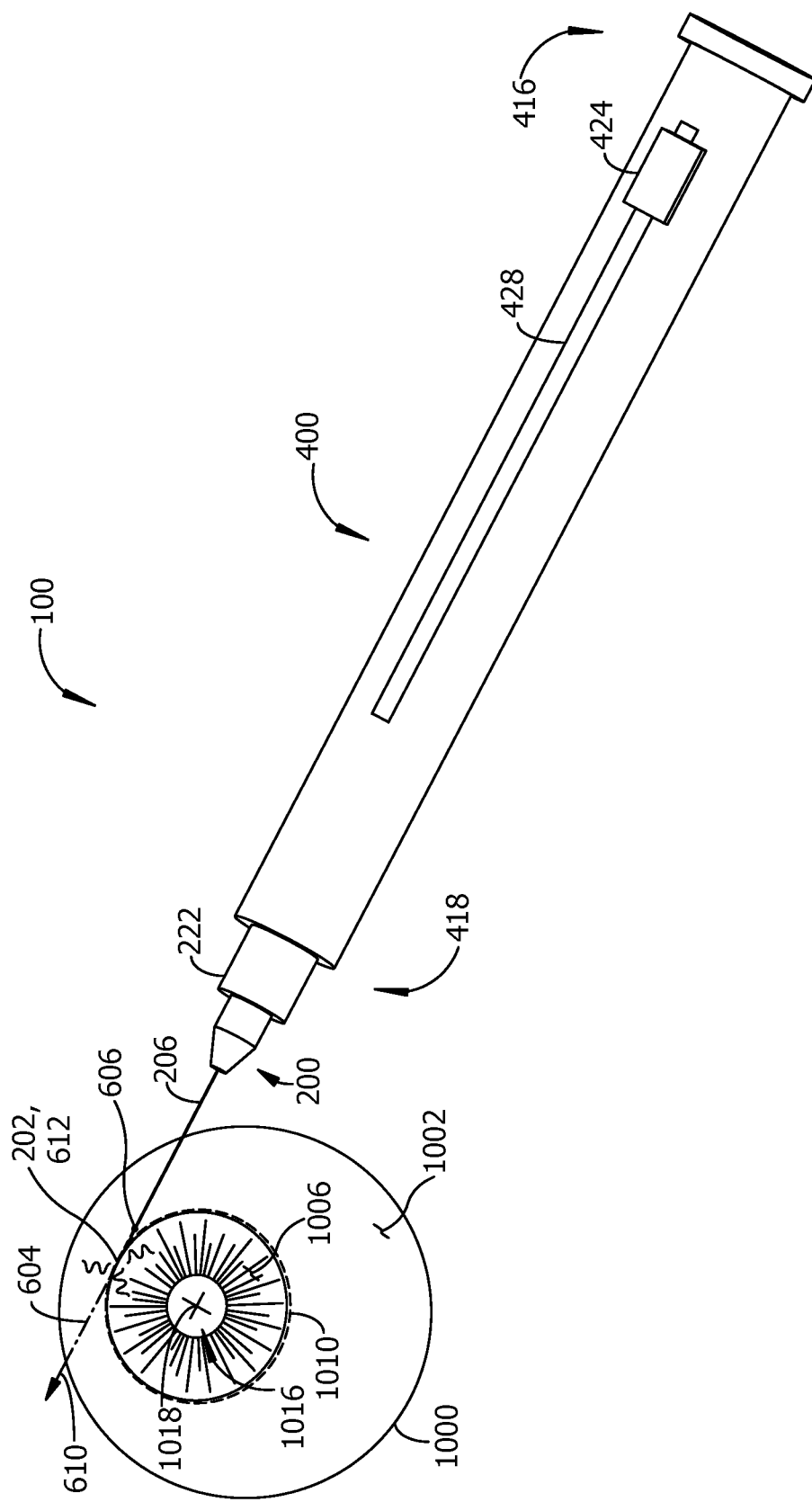
FIG. 21 shows a pictorial view of an example microsurgical instrument embodiment including a positioner with the distal tip of the trocar passing through the sclera of an eye into Schlemm's canal, illustrating an example of light emitted from the illuminated distal end of the trocar to accurately indicate the position of the trocar.
Figure 22:
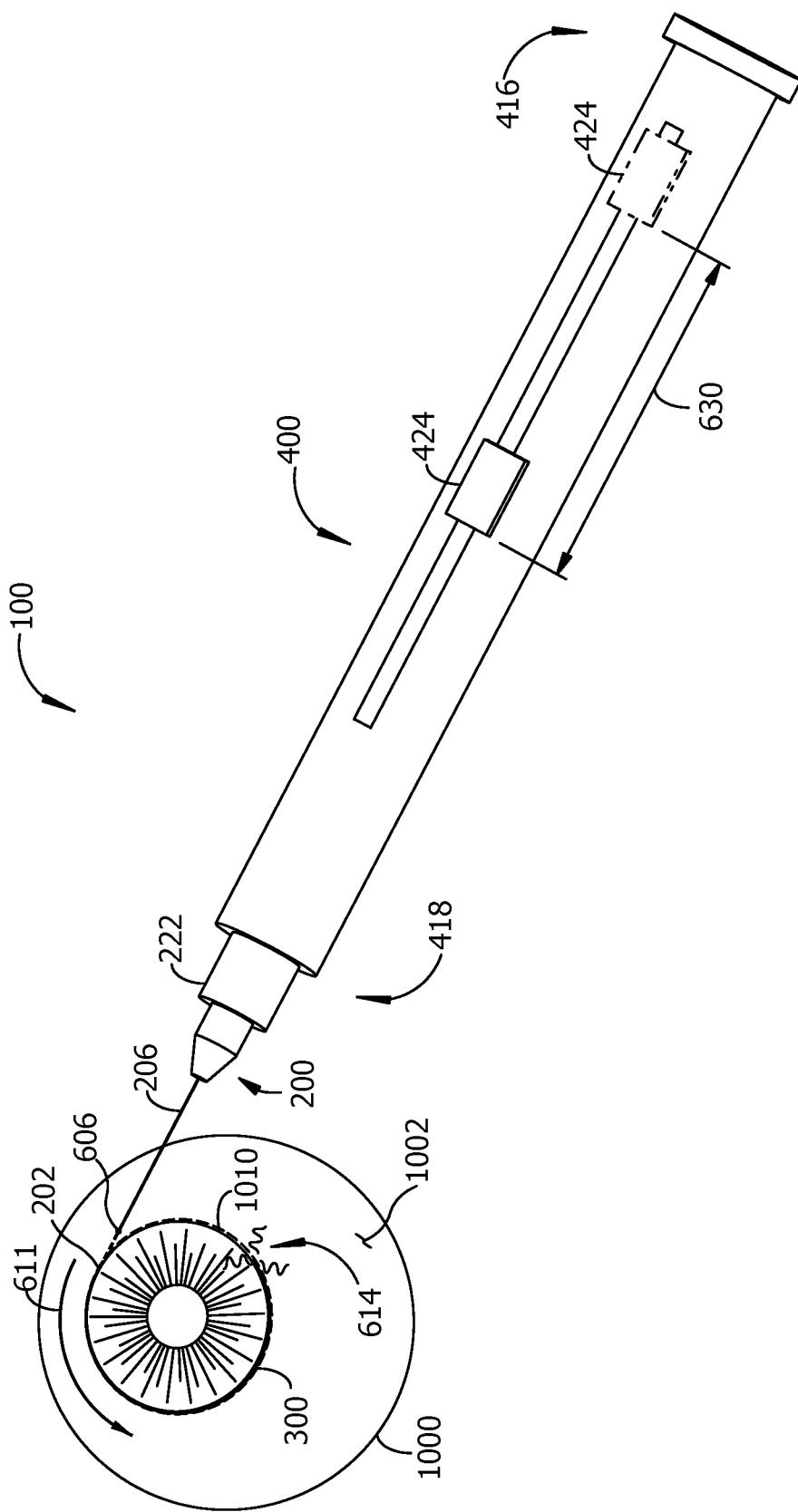
FIG. 22 shows a pictorial view with the example microsurgical instrument and trocar in the same position relative to Schlemm's canal as in FIG. 21, and further illustrating an example of the illuminated distal tip of the composite microcannula extended outward from the trocar along the circumferential path of Schlemm's canal.

FIGS. 21 and 22 illustrate an example of a location of a trocar entry point on an eye and extension of the composite microcannula to follow the circumferential path of Schlemm's canal. FIGS. 21 and 22 both show a pictorial view of the positioner 400 in a same position and orientation relative to an eye 1000. Other parts of the approximately spherical eye 1000 shown in simplified form in the figures include the sclera 1002, the iris 1006, the pupil 1016, and the circumferential path of Schlemm's canal 1010 near the limbus of the eye. Schlemm's canal 1010 includes a porous, approximately circular drainage channel receiving aqueous humor flowing through the trabecular meshwork near the outer edge of the iris. Schlemm's canal is marked in the figures with a hidden line to represent the canal's approximate position behind the exterior surface of the sclera 1002. The cornea, extending outward toward the viewer above the iris 1006, may be considered to be present in FIGS. 21 and 22, but is transparent and is not marked. A center 1018 of the pupil 1016 also indicates the approximate center of the iris 1006.

In the example of FIGS. 21 and 22, the distal end 202 of the trocar 200 has been inserted into the sclera 1002 at a preferred trocar entry point 606, puncturing the sclera with a small hole having a diameter about the same as the outer diameter of the rigid hollow shaft 206. The trocar may be advanced in a direction 610 along a line 604 tangent to Schlemm's canal 1010. In the example of FIG. 21, the distal end 202 of the trocar 200 is positioned as having just entered the interior of Schlemm's canal 1010. The position of the distal end of the trocar is made visible by light 612 radiating from the lumen of the trocar. In some embodiments 100, the light 612 will have been emitted from the distal end of a light guide with the end of the light guide offset a selected distance 626 from the distal end of the trocar lumen 208 (ref. FIG. 12). Light 612 radiating from the interior of Schlemm's canal through the sclera may have the visual appearance from outside the eye of a bright spot on the exterior of the eye, and this light radiating from the interior of Schlemm's Canal through the Trabecular Meshwork may have the visual appearance of a well-defined bright spot visible across the anterior chamber of the eye. The bright spot is a visual indication of the precise position of the distal end 202 of the trocar 200. Light 612 emitted from the end of the trocar and light 614 emitted from the end of the composite microcannula are represented by short wavy lines in the figures. A gonioprism may be used to view the bright spots marking the positions of the trocar and composite microcannula.

An example of a preferred entry point 606 of the trocar 200 through the sclera is shown in FIG. 21 along a line 604 tangent to Schlemm's canal. The entry point 606 of the trocar 200 into the sclera 1002 may be offset a predetermined distance from the limbus on the tangent line 604. The offset distance may be selected to cause the trocar to pass into the interior of Schlemm's canal when inserted at the preferred entry point 606 with the shaft 206 of the trocar parallel to the tangent line. A trocar entry point marking instrument may be used to mark the surface of an eye with the preferred entry point 606 and direction of advance for the trocar along a tangent line 604, as will be explained in more detail with regard to FIGS. 26-29.

The actuator 424 on the example of a positioner 400 is shown near the proximal end of the actuator's range of travel in FIG. 21. As the actuator is moved from its position in FIG. 21 in a distal direction to the position shown in FIG. 22, the microcannula displacement mechanism 425, which may include the examples of the actuator block 426 and the hollow sleeve 433 from the positioner embodiment 400 of FIG. 20, causes the composite microcannula to extend outward from the distal end of the trocar. The example of a displacement distance 630 in FIG. 22 corresponds to a length of the portion of the composite microcannula extending outward from the distal end of the trocar by movement of the actuator 424.

In the example of FIG. 22, the segment of the composite microcannula extending outward from the distal end 202 of the trocar 200 follows the circumferential path of Schlemm's canal 1010 in a counterclockwise direction 611 from the trocar entry point 606. Light 614 emitted from the distal end of the composite microcannula 300 may be visible through the sclera as a small spot of light, accurately indicating the position of the distal end of the composite microcannula. The composite microcannula could alternately be made to follow Schlemm's canal in a counterclockwise direction by reorienting the positioner 400. Should the composite microcannula deviate from a preferred path, for example leaving Schlemm's canal and entering a collector channel, the path change will quickly become apparent because of the illuminated distal tip of the microcannula.

The positioner 400 may remain stationary relative to the eye 1000 while the composite microcannula moves through Schlemm's canal or other parts of the eye. The positioner 400 may hold the composite microcannula stationary relative to the eye, for example while a payload is being delivered through the composite microcannula to a target region in the eye. Although the examples of a trocar in FIGS. 19-22 do not include finger grips, the examples apply also to a trocar with a finger grip. A finger grip may be used to immobilize the positioner, for example by holding the finger grip to a patient's skin with adhesive tape or a temporary stitch.

Some embodiments of a trocar are configured to receive two light guides. One of the light guides may be included in a composite microcannula as previously described. The second light guide may be in another composite microcannula or may be provided independently of a composite microcannula. Examples of a trocar adapted for two light guides are shown in FIGS. 23 and 24. In the example of FIG. 23, the composite microcannula 300 is shown with its distal end 308 extending out from the distal end 202 of the trocar 200, and with light 614 being emitted from the light guide in the composite microcannula. An optional second light guide 412 is also positioned in the lumen of the trocar 200, with the distal end 413 of the second light guide 412 remaining inside the trocar, radiating light 612 from the distal end of the trocar. As suggested in FIG. 24, the two light guides may optionally selectively illuminate the distal end 202 of the trocar 200 only, the distal end 326 of the composite microcannula only, or both, either sequentially or simultaneously. The emitted light (612, 614) may optionally have a wavelength and/or intensity not visible to unaided human vision.

An optional camera 616 may be provided to capture images of the emitted light (612, 614) passing through eye tissue from the trocar and/or microcannula. The positions of the composite microcannula and trocar may be visible in an image from the camera 616 presented on a computer monitor, smart phone display, and/or instrument display. In some microsurgical instrument embodiments 100, the composite microcannula 300 and the second light guide 412 may both receive light from the same light source. The composite microcannula may be advanced until it reaches a target region 1014, for example an area to be cleared of an obstruction or constriction, or an area that will receive a payload delivered through the composite microcannula.

Figure 25:
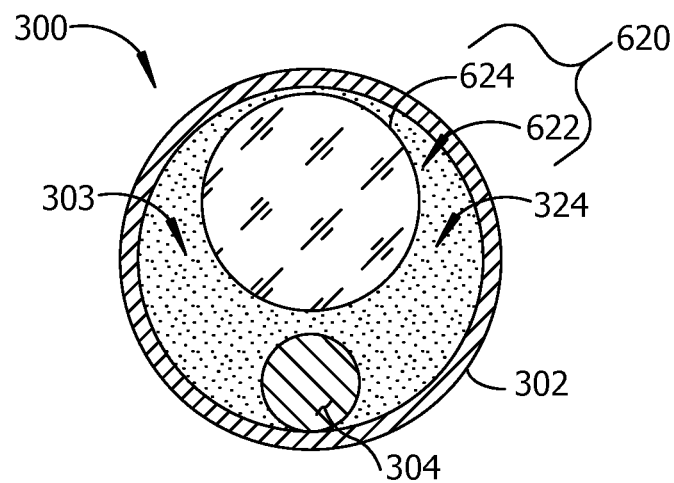
FIG. 25 shows an alternative cross-sectional view D-D of an example of a composite microcannula embodiment carrying an example of an optional fluid payload and an example of an optional solid payload inside the flexible hollow tube.

FIG. 25 shows an example of a payload 620 carried in the void 303 inside the flexible hollow tube 302 of a composite microcannula 300. The payload may follow the fluid path 324 through the composite microcannula. The composite microcannula may therefore be used to precisely position the payload in a target region of an eye. The payload 620 may be a solid object 624, a fluid 622, for example a fluid comprising a gas and/or a liquid, or both a solid object and a fluid. The fluid may optionally be used to transport a solid object 624, or a long solid payload may be pushed in from the proximal end of the composite microcannula until the payload extends out the distal end of the composite microcannula. The example of a composite microcannula 300 in FIG. 25 has a light guide 304 inside the flexible hollow tube. Other embodiments of a composite microcannula 300 disclosed herein may also be used to deliver a payload 620.

Figure 26:
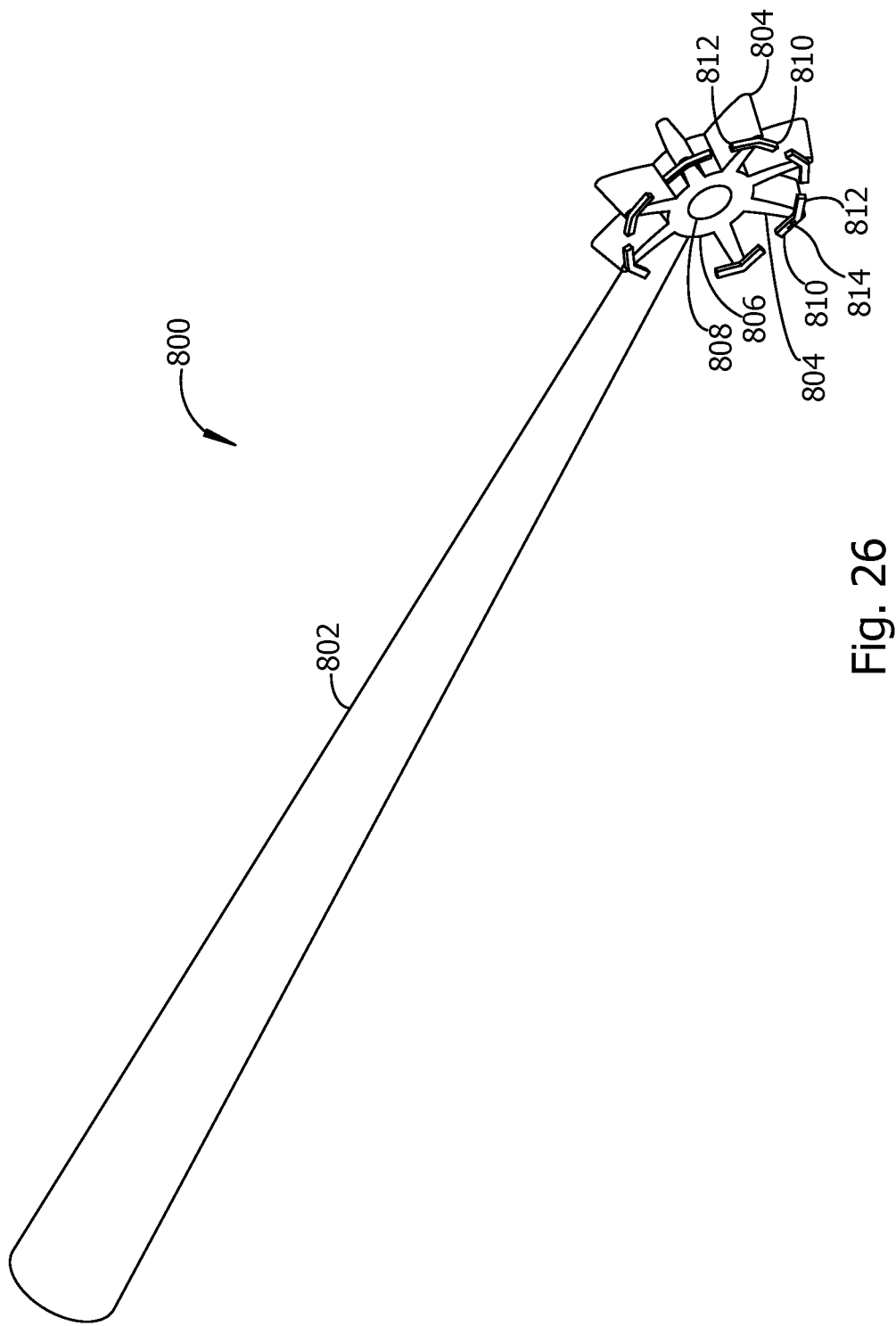
FIG. 26 shows a pictorial view of an example of a trocar entry point marking instrument.
Figure 27:
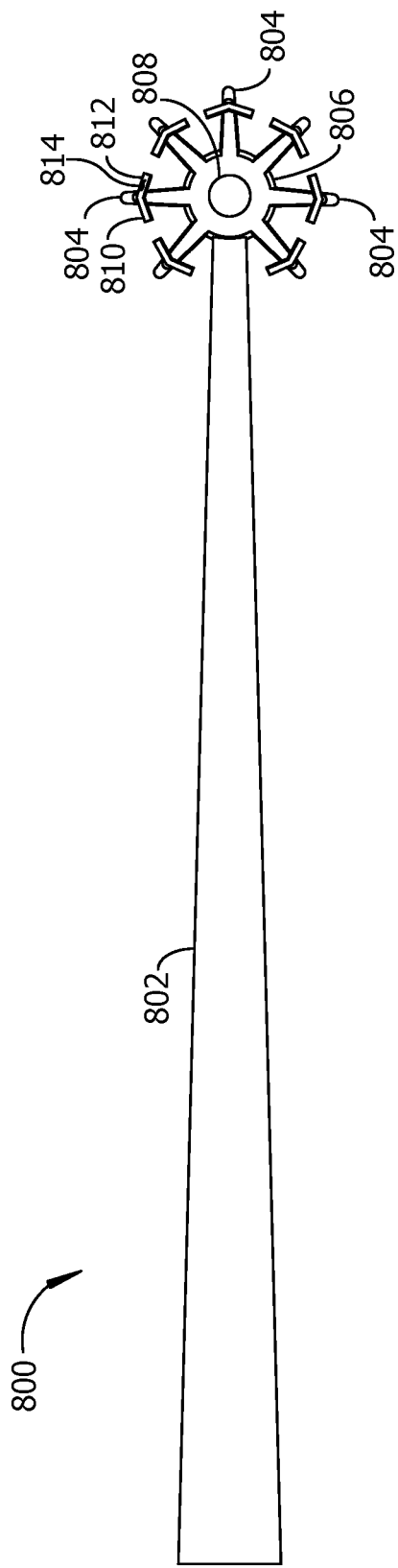
FIG. 27 shows a view toward examples of marking surfaces on marking pads on the trocar entry point marking instrument of FIG. 26.
Figure 28:
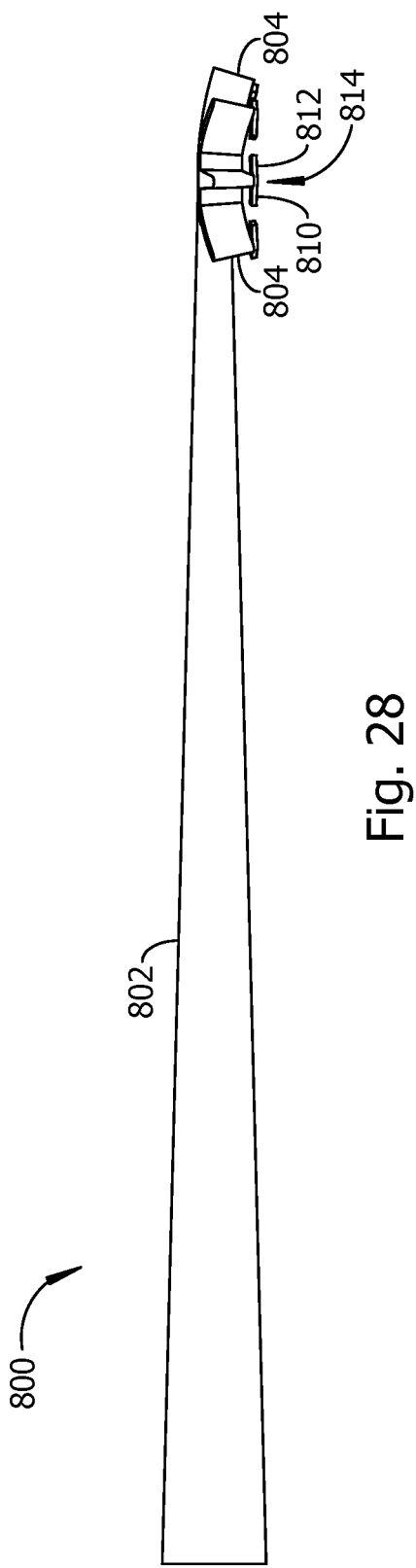
FIG. 28 shows a side view of the example trocar entry point marking instrument of FIGS. 26-27.

FIGS. 26, 27, and 28 show an example of a trocar entry point marking instrument 800, also referred to as a marking jig 800. The marking instrument may be used to form a pattern of tangent lines on the sclera of an eye. The pattern of lines marks at least one, and optionally more than one, preferred trocar entry point and preferred trocar insertion direction for guiding a trocar 200 through the sclera into the interior fluid passage in Schlemm's canal. The marking instrument 800 includes at least one pair of marking pads 810, 812. Each marking pad 810, 812 is preferably positioned to form a line tangent to Schlemm's canal when an edge 808 of a sighting aperture through a hub 806 is concentric with the pupil of the eye. A dye applied to a contact surface 814 on each marking pad 810, 812 may be transferred to the sclera 1002 as intersecting line segments when the contact surfaces touch the surface of the eye.

The two marking pads 810, 812 in each pair are disposed at an angle to one another such that the intersection of the two line segments formed on the eye marks the location of the preferred trocar entry point 606. The intersection point of the two line segments is preferably offset by a predetermined separation distance 826 from the limbus 1008, measured in a radial direction from the center 1018 of the pupil. The limbus 1008 indicates the underlying position of Schlemm's canal 1010 with sufficient precision for the markings made by the two pads 810, 812 to accurately indicate the insertion position and direction of the distal end of the trocar for entry into Schlemm's canal. The predetermined separation distance may be determined from a selected length of each line segment to be marked on the eye and from the number of separate trocar entry points 606 to be marked on the eye.

The pairs of pads 810, 812 may be connected to a central hub 806. A handle 802 may be attached to the central hub 806. The pads 810, 812 may be connected directly to the hub, or may alternatively be connected to the hub by an intervening radial arm 804. The example of a trocar entry point marking instrument 800 in FIG. 26 includes a hub 806 with seven radial arms 804. A first marking pad 810 and a second marking pad 812 disposed at an angle to the first marking pad are connected to each radial arm 804. An alternative embodiment of a marking jig 800 may have a different number of radial arms and marking pads than are shown in the figures.

Figure 29:
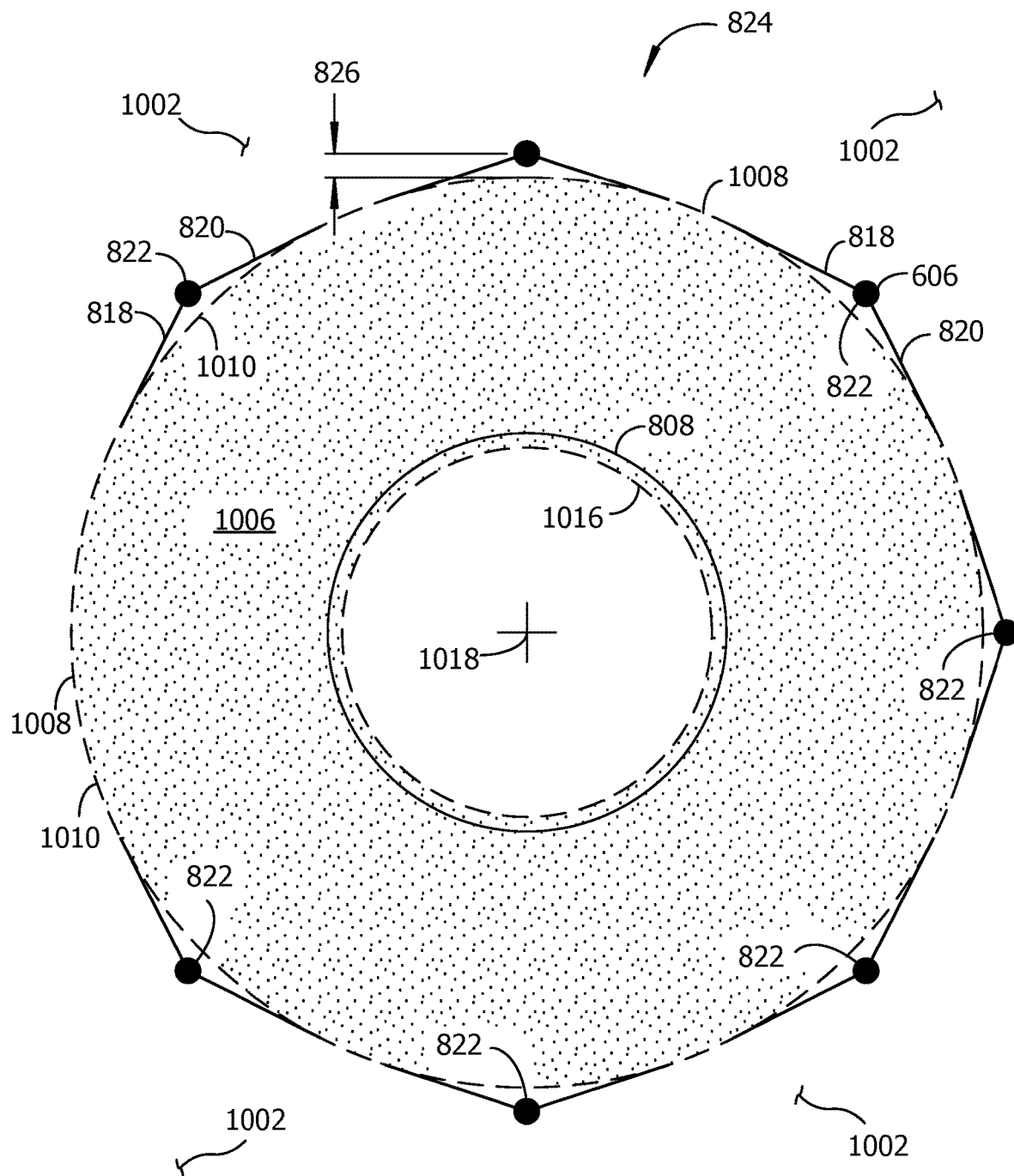
FIG. 29 shows a view toward an example of the sclera and iris of a human eye, illustrating an example of a pattern of tangent lines formed by the trocar entry point marking instrument of FIGS. 26-28.

FIG. 29 shows an example of trocar entry point markings made on the exterior surface of an eye by the marking instrument 800 of FIGS. 26-28. In the example of FIG. 29, the iris 1006 is represented as a shaded area between the edge of the pupil 1016 and the limbus 1008, with Schlemm's canal 1010 close to the limbus. The limbus 1008, Schlemm's canal 1010, and edge of the pupil 1016 are represented in FIG. 29 by dashed lines to distinguish these lines from markings made by the instrument 800. The sclera 1002 is represented in FIG. 29 by areas outside the perimeter of the limbus 1008.

Each pair of marking pads 810, 812 prints a corresponding pair of line segments 818, 820 tangent to Schlemm's canal 1010. Each pair of line segments 818, 820 meets at an intersection point 822 corresponding to a trocar entry point 606 on the sclera. More than one entry point 606 may be marked to provide a choice of trocar insertion points for reaching a target area in an eye. Each intersection point 822 is offset in a radial direction from the limbus 1008 by the predetermined separation distance 826. A dot or other marking may be placed at each intersection point 822 to enhance visibility of the positions of the trocar entry points 606.

After the trocar entry point marking instrument 800 transfers the pattern of intersection line segments from the example of FIG. 29 to the surface of the eye, one of the intersection points 822 may be selected for insertion of the trocar through the sclera. The distal end 210 of the trocar 200 is preferably placed in direct contact with the intersection point 822 on the sclera. The shaft 206 of the trocar is preferably made parallel to one of the line segments 818, 820 and the trocar advanced parallel to the line segment in the direction from the intersection point 822 to the limbus 1008 until the illuminated distal end 220 of the trocar is observed to enter Schlemm's canal 1010. After the trocar enters Schlemm's canal, the composite microcannula 300 may be extended from the end of the trocar as described for the examples of FIGS. 21 and 22.

Figure 30:
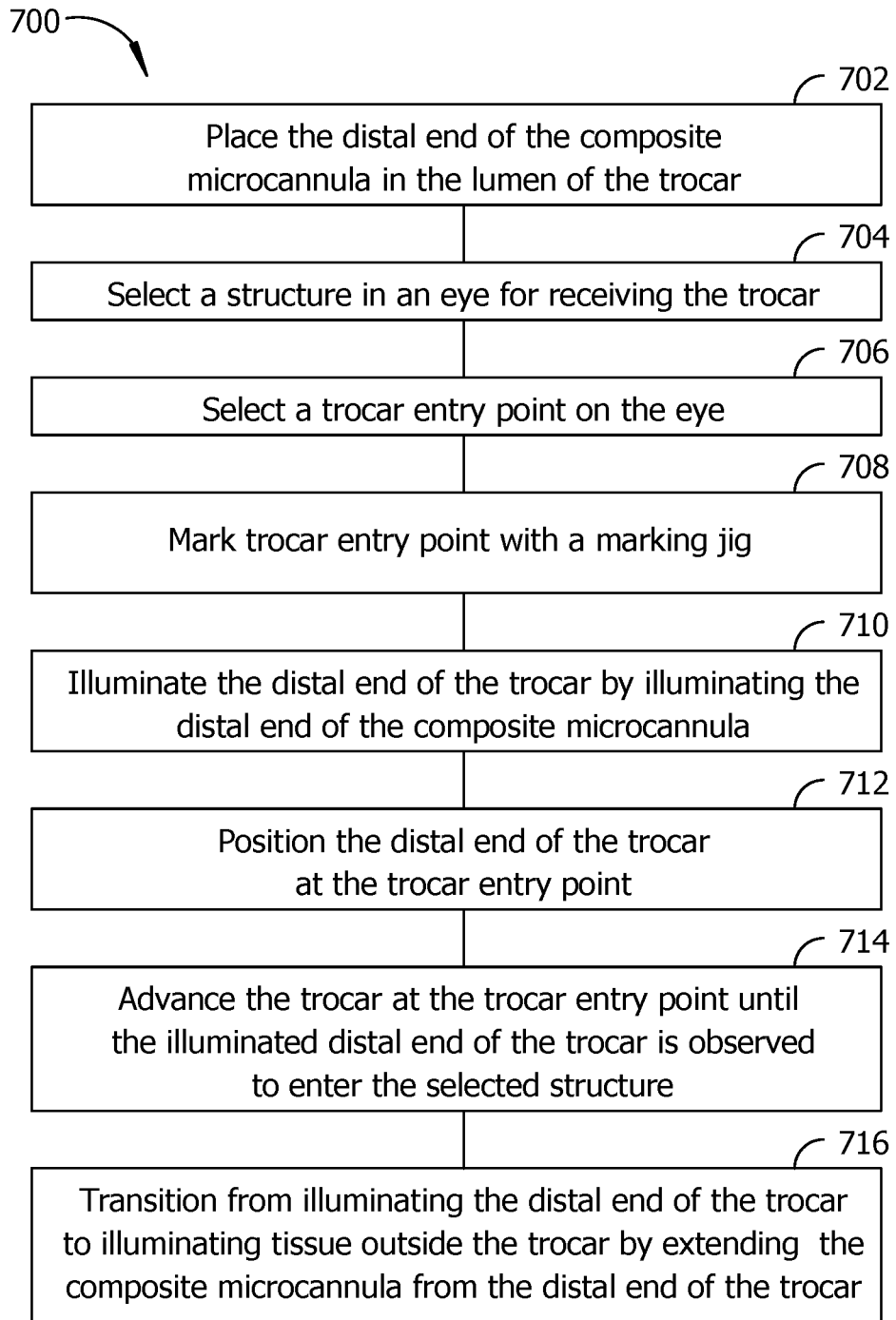
FIG. 30 illustrates an example of some steps included in a method for inserting a trocar through the sclera of an eye and advancing a composite microcannula from the trocar into a structure such as Schlemm's canal.

FIG. 30 shows an example of some steps included with a method embodiment. A method in accord with an embodiment 700 may include any one or more of the following steps, in any combination:

at step 702, placing a distal end of a composite microcannula within a lumen of a trocar; and at step 704, selecting a structure in an eye for receiving the trocar. Schlemm's canal, a collector channel, and a blood vessel are examples of structures which may be selected, but it will be appreciated that embodiments of the microsurgical instrument 100 may be used to introduce a composite microcannula into other chambers, vessels, or channels in an eye or another organ.

The example of a method embodiment may further include:

at step 706, selecting a trocar entry point on an eye;

at optional step 708, marking a trocar entry point with a marking jig, for example the trocar entry point marking instrument 800 in the example of FIG. 26;

at step 710, illuminating the distal end of the composite microcannula, thereby illuminating the distal end of the trocar;

at step 712, positioning the trocar at the selected trocar entry point;

at step 714, advancing the trocar from the selected trocar entry point until the illuminated distal end of the trocar is observed to enter the selected structure in the eye; and at step 716, extending the composite microcannula from the distal end of the trocar toward a target region in the eye, thereby transitioning from illuminating the distal end of the trocar to illuminating tissue outside the trocar. Examples of a target region include, but are not limited to, a chamber, vessel, channel or canal blocked by obstructing material, and a collapsed or constricted space to be enlarged or re-opened.

The example method embodiment may optionally include any one or more of:

holding the distal end of the composite microcannula stationary relative to the trocar;

selecting Schlemm's canal as the structure to be entered by the illuminated distal end of the trocar;

advancing the trocar from the selected trocar entry point along a line tangent to Schlemm's canal;

marking the trocar entry point at the intersection of two lines, each of the two lines tangent to Schlemm's canal;

positioning the two tangent lines to intersect a preferred distance from the limbus of an eye;

centering a marking instrument over the pupil of an eye and pressing the marking instrument against the eye to mark the two tangent lines onto the surface of the eye;

marking more than one trocar entry point each time the marking instrument is pressed against the eye;

illuminating the distal end of the trocar with another light guide;

inserting a payload into the composite microcannula and delivering the payload to the target region;

illuminating the distal end of the trocar with electromagnetic radiation having a wavelength not visible to unaided human vision and observing the distal end of the trocar with a camera sensitive to the electromagnetic radiation;

withdrawing the composite microcannula through the trocar while keeping the trocar at the trocar entry point;

inserting a payload into the composite microcannula;

moving the payload through the composite microcannula to the target region;

retracting the composite microcannula with the payload remaining in the target region; and keeping the trocar stationary relative to the eye after the distal end of the trocar enters the selected structure in the eye.

Figure 34:
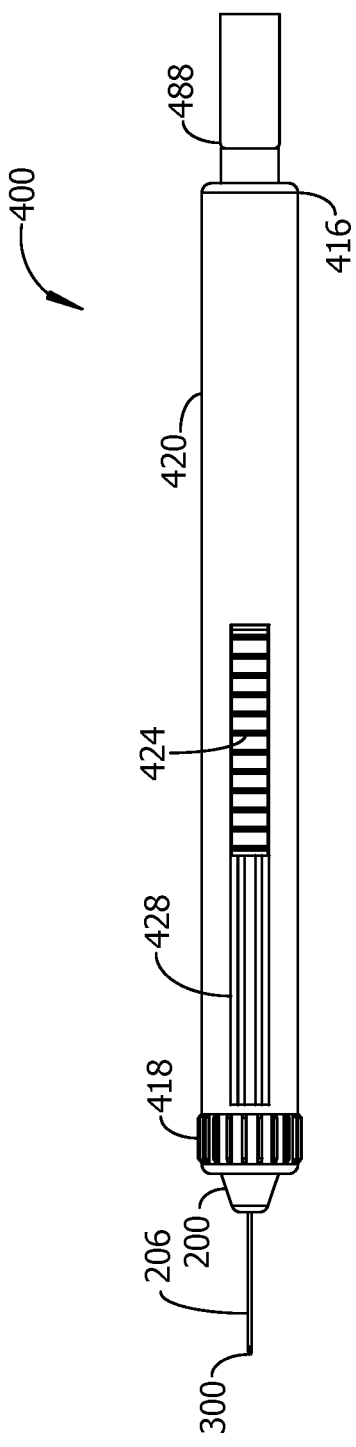
FIG. 34 is a view toward a top side of another an example of a microsurgical instrument embodiment with a positioner and a trocar.
Figure 35:
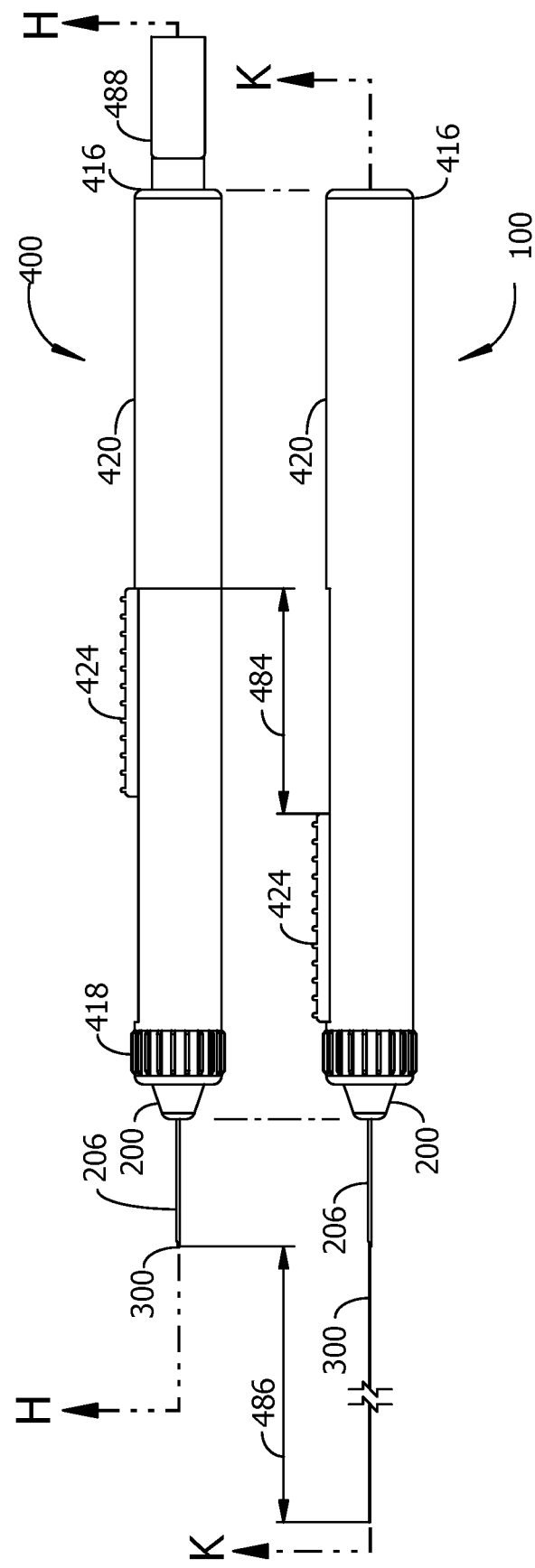
FIG. 35 is a side view of two of the microsurgical instrument examples of FIG. 34, with the upper device showing the composite microcannula in an example of a retracted position and the lower device showing the composite microcannula in an example of an extended position.
Figure 36:
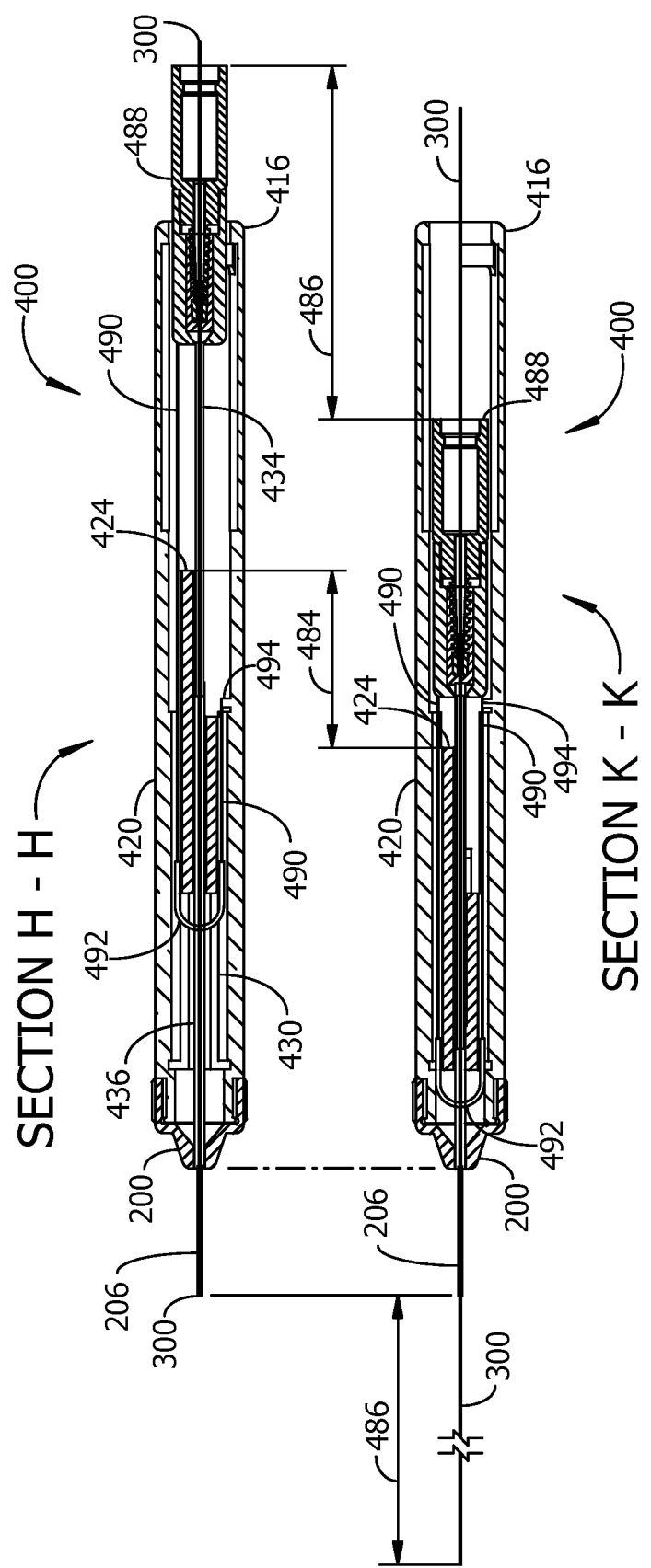
FIG. 36 continues the example of FIGS. 34-35, showing the examples of a microsurgical instrument in cross-sectional view H-H for the retracted position of the composite microcannula and cross-sectional view K-K for the extended position of the composite microcannula. The positions of cross sections H-H and K-K are marked by section lines H-H and K-K in FIG. 35.

FIGS. 34, 35, and 36 show another example of a microsurgical instrument having a positioner configured for extending and retracting a composite microcannula through the lumen of a trocar. The positioner 400 is configured for attachment of a trocar 200 to the distal end 418 of a handpiece 420. The composite microcannula 300 passes through the lumen of the trocar 300 and through the handpiece 420, where the microcannula is coupled to an insert 488 slidably engaged with the handpiece 420. As will be explained in more detail below, sliding an actuator 424 in a slot 428 on the handpiece 420 by a selected distance 484 causes a corresponding displacement of the composite microcannula with respect to the end of the trocar's rigid hollow shaft 206 by a distance 486 equal to twice the displacement distance 484 of the actuator. The trocar 200 and the composite microcannula 300 may be provided separately from the positioner 400 and may be removable for replacement should either the trocar or microcannula become damaged, contaminated, or otherwise unusable for a particular procedure.

Some internal features of the example positioner 400 of FIG. 34 are shown in two cross-sectional views in FIG. 36. Section H-H in FIG. 36 shows the actuator 424 retracted toward the proximal end 416 of the handpiece 420. Section J-J shows the actuator advanced toward the distal end 418 of the handpiece 420. The two views of the handpiece 420 are referenced to one another in FIG. 36 so that the positions of internal components may be accurately compared between the cross-sections.

The insert 488 is slidably engaged with the interior surface of a void formed inside the handpiece 420. The actuator 424 travels along one or more guide ridges 430. A U-shaped hollow tube 492 attached to the actuator 424 moves with the actuator. An insert displacement wire 490 passes slidably through the lumen of the U-shaped hollow tube 492. One end of the insert displacement wire 490 is affixed to the insert 488. The opposite end of the insert displacement wire 490 is affixed to an anchor post 494 strongly attached to, or alternately formed as an integral part of, the handpiece 420. The insert displacement wire 490 is preferably flexible enough to slide easily around the bend in the U-shaped hollow tube 492, yet stiff enough to push the insert 488 in a distal direction (i.e., away from the trocar 200) when the actuator is displaced in a distal direction.

With one end of the insert displacement wire 490 fixed to the handpiece at the anchor post 494 and the other end of the wire fixed to the insert 488, a sliding displacement of the actuator 424 along the handpiece by a distance "d" 484 causes the U-shaped hollow tube 492 to be displaced by the same distance "d" and the insert 488 to be displaced by twice as much (2×d), represented in the figures by a relative displacement 486 of the insert between cross sections H-H and K-K. The composite microcannula 300 is coupled to the insert 488 sufficiently strongly to keep the composite microcannula stationary relative to the insert when the actuator is moved relative to the handpiece. Because the insert moves twice the displacement distance 484 of the actuator, the composite microcannula also moves twice the displacement distance 484 of the actuator. Moving the actuator proximally by a distance "d" 484 extends the composite microcannula from the trocar by a distance "2×d" 486. Moving the actuator distally by a distance "d" retracts the composite microcannula by a distance "2×d".

The composite microcannula 300 may pass through a hollow sleeve having a fixed segment 436 attached to, or alternately formed as an integral part of, the rigid hollow shaft 206 of the trocar 200. A movable segment 434 of the hollow sleeve is slidably engaged with the fixed segment 436 at one end and attached to the insert 488 at the other end. The hollow sleeve limits transverse deflection of the composite microcannula as the actuator is advanced and retracted, forcing the composite microcannula to extend and retract without kinking or significant bending inside the handpiece.

As suggested in the example of FIG. 36, the composite microcannula 300 may extend outward from the proximal end 416 of the positioner 400 and insert 488. The proximally-extending portion of the composite microcannula may be configured to receive solid and/or liquid payloads, surgical instruments, and one or more optical fibers as previously described.

Unless expressly stated otherwise herein, ordinary terms have their corresponding ordinary meanings within the respective contexts of their presentations, and ordinary terms of art have their corresponding regular meanings.

What is claimed is:

1. An apparatus, comprising:
   a trocar comprising a rigid shaft having a proximal end and a distal end, said rigid shaft formed with a lumen extending from said proximal end through said distal end, said distal end shaped to puncture a sclera of an eye;
   a composite microcannula positioned in said lumen, comprising:
      a flexible hollow tube having an outer diameter less than an inner diameter of said lumen; and
      a layer of material within said flexible hollow tube, said layer of material surrounding a lumen of said flexible hollow tube, said layer of material formed as a light guide having a different index of refraction from an index of refraction of said flexible hollow tube for transmitting light coupled into a proximal end of said composite microcannula to a distal end of said composite microcannula during extension of said composite microcannula beyond said distal end of said rigid shaft,
      wherein said composite microcannula is controllably extendable beyond said distal end of said trocar further into the eye after puncture of the sclera has been achieved;
   a handpiece;
   an actuator slidably coupled to said handpiece;
   an insert slidably coupled to said handpiece;
   a hollow tube attached to said actuator; and
   a wire passing through said hollow tube, a first end of said wire attached to said handpiece and a second end of said wire attached to said insert.

2. The apparatus of claim 1, further comprising said flexible hollow tube formed with a void space extending from a proximal end of said composite microcannula to a distal end of said composite microcannula, and said layer of material disposed concentrically around said void space inside said flexible hollow tube.

3. The apparatus of claim 1, further comprising said trocar attached to said handpiece.

4. The apparatus of claim 3, further comprising said composite microcannula coupled to said insert.

5. The apparatus of claim 4, further comprising a movable sleeve slidably engaged with said rigid shaft, said movable sleeve attached to said insert, and said composite microcannula passing through said movable sleeve.

6. The apparatus of claim 1, wherein said hollow tube is generally U-shaped.

7. The apparatus of claim 1, wherein said composite microcannula has an outer diameter and a flexural rigidity configured to enable said composite microcannula to follow a Schlemm canal.

8. An apparatus, comprising:
   a trocar comprising a rigid shaft having a proximal end and a distal end, said rigid shaft formed with a lumen extending from said proximal end through said distal end, said distal end shaped to puncture a sclera of an eye;
   a composite microcannula positioned in said lumen, comprising:
      a flexible hollow tube having an outer diameter less than an inner diameter of said lumen; and
      a layer of material within said flexible hollow tube, said layer of material having a different index of refraction from an index of refraction of said flexible hollow tube, wherein said composite microcannula is controllably extendable beyond said distal end of said trocar further into the eye after puncture of the sclera has been achieved;

a handpiece;

an actuator slidably coupled to said handpiece;

an insert slidably coupled to said handpiece;

a hollow tube attached to said actuator; and a wire passing through said hollow tube, a first end of said wire attached to said handpiece and a second end of said wire attached to said insert.

9. The apparatus of claim 8, further comprising said trocar attached to said handpiece.

10. The apparatus of claim 8, further comprising said composite microcannula coupled to said insert.

11. The apparatus of claim 8, further comprising a movable sleeve slidably engaged with said rigid shaft, said movable sleeve attached to said insert, and said composite microcannula passing through said movable sleeve.

12. The apparatus of claim 8, wherein said hollow tube is generally U-shaped.

\* \* \* \* \*